United States Patent
Tsuruoka

(10) Patent No.: US 8,805,061 B2
(45) Date of Patent: Aug. 12, 2014

(54) SIGNAL PROCESSING SYSTEM AND SIGNAL PROCESSING PROGRAM

(75) Inventor: Takao Tsuruoka, Machida (JP)

(73) Assignee: Olympus Corporation, Tokyo (JP)

( * ) Notice: Subject to any disclaimer, the term of this patent is extended or adjusted under 35 U.S.C. 154(b) by 346 days.

(21) Appl. No.: 12/953,740

(22) Filed: Nov. 24, 2010

(65) Prior Publication Data

US 2011/0069868 A1     Mar. 24, 2011

Related U.S. Application Data

(63) Continuation of application No. PCT/JP2009/059551, filed on May 25, 2009.

(30) Foreign Application Priority Data

May 28, 2008    (JP) .................................. 2008-139930

(51) Int. Cl.
*G06K 9/00*          (2006.01)
*H04N 9/47*          (2006.01)
*H04N 7/18*          (2006.01)
*A61B 1/04*          (2006.01)

(52) U.S. Cl.
USPC .............. 382/162; 382/128; 348/65; 600/109

(58) Field of Classification Search
USPC ...................... 382/128, 162; 348/65; 600/109
See application file for complete search history.

(56) References Cited

U.S. PATENT DOCUMENTS

| | | | |
|---|---|---|---|
| 4,885,634 A | 12/1989 | Yabe | |
| 5,550,582 A | 8/1996 | Takasugi et al. | |
| 5,995,645 A | 11/1999 | Soenksen et al. | |
| 6,750,964 B2 | 6/2004 | Levenson et al. | |
| 7,136,518 B2 | 11/2006 | Griffin et al. | |
| 7,321,791 B2 | 1/2008 | Levenson et al. | |

(Continued)

FOREIGN PATENT DOCUMENTS

| | | |
|---|---|---|
| EP | 1 880 658 A1 | 1/2008 |
| JP | 6-335451 A | 12/1994 |

(Continued)

OTHER PUBLICATIONS

Ruifrok, A.—"Quantification of Histochemical Staining by Color Deconvolution"—The International Academy of Cytology Analytical and Quantitative Cytology and Histology—Aug. 2001, pp. 291-299.*

(Continued)

*Primary Examiner* — Bernard Krasnic
(74) *Attorney, Agent, or Firm* — Holtz Holtz Goodman & Chick PC

(57) ABSTRACT

A dedicated base vector based on a known spectral characteristic of a subject as an identification target having the known spectral characteristic and a spectral characteristic of an imaging system, which includes a spectral characteristic concerning a color imaging system used for image acquisition of subjects including the subject as the identification target and a spectral characteristic concerning illumination light used when image acquisition of the subjects by the color imaging system, are acquired. A weighting factor concerning the dedicated base vector is calculated based on an image signal obtained by image acquisition of the subject by the color imaging system, the dedicated has vector, and the spectral characteristic of the imaging system. An identification result of the subject which is the identification target having the known spectral characteristic is calculated based on the weighting factor concerning the dedicated base vector to output as an output signal.

24 Claims, 25 Drawing Sheets

(56) References Cited

U.S. PATENT DOCUMENTS

| | | | |
|---|---|---|---|
| 7,720,272 B2 | 5/2010 | Armogida | |
| 7,916,943 B2 | 3/2011 | Ohara et al. | |
| 8,532,376 B2 * | 9/2013 | Tsuruoka | 382/165 |
| 2002/0054237 A1 * | 5/2002 | Nichogi | 348/453 |
| 2003/0038954 A1 * | 2/2003 | Odagiri et al. | 358/1.9 |
| 2004/0202356 A1 | 10/2004 | Stookey et al. | |
| 2006/0103728 A1 * | 5/2006 | Ishigami et al. | 348/180 |
| 2007/0153370 A1 | 7/2007 | Olszak et al. | |
| 2008/0079803 A1 | 4/2008 | Sekiguchi | |
| 2008/0194972 A1 | 8/2008 | Gono | |
| 2008/0212865 A1 | 9/2008 | Zhu et al. | |
| 2009/0023991 A1 | 1/2009 | Gono et al. | |
| 2009/0058999 A1 | 3/2009 | Gono et al. | |
| 2009/0096889 A1 * | 4/2009 | Tsuruoka | 348/222.1 |
| 2009/0202131 A1 | 8/2009 | Armogida | |
| 2010/0014753 A1 * | 1/2010 | Tsuruoka | 382/165 |
| 2010/0094136 A1 | 4/2010 | Nakaoka et al. | |

FOREIGN PATENT DOCUMENTS

| | | | |
|---|---|---|---|
| JP | 2003-93336 A | 4/2003 | |
| JP | 2005-181276 A | 7/2005 | |
| JP | 2006-314557 A | 11/2006 | |
| JP | 2006-341077 A | 12/2006 | |
| JP | 2006-341078 A | 12/2006 | |
| JP | 2007-111357 A | 5/2007 | |
| JP | 2008-128982 A | 6/2008 | |
| JP | 2008-161550 A | 7/2008 | |
| JP | 2009-285084 A | 12/2009 | |
| WO | WO 2006/120798 A1 * | 11/2006 | G01N 21/27 |
| WO | WO 2007/148576 A1 * | 12/2007 | H04N 9/09 |

OTHER PUBLICATIONS

International Preliminary Report on Patentability (IPRP) dated Jan. 20, 2011 in International Application No. PCT/JP2009/059551.
International Search Report and Written Opinion dated Aug. 18, 2009 (in English) in counterpart International Application No. PCT/JP2009/059551.
Extended European Search Report (EESR) dated May 30, 2012 (in English) in counterpart European Application No. 09754665.9.
Breiteenbach Karl-Heniz: "MS-DOS and MS-Windows are PC Standards": Computer Standards & Interfaces 8 (1988): pp. 41-44.
U.S. Appl. No. 12/504,202; First Named Inventor: Takao Tsuruoka ; Title: "Signal Processing System and Computer Readable Medium for Recording Signal Processing Program"; filed Jul. 16, 2010.
Japanese Office Action dated Jan. 11, 2011 (and English translation thereof) in counterpart Japanese Application No. 2008-187692.
Extended European Search Report dated Nov. 3, 2010 (in English) in counterpart European Application No. 09009352.7.
Bautista P A et al.: "Digital Staining of Unstained Pathological Tissue Samples through Spectral Transmittance Classification": Optical Review: vol. 12, No 1: (Jan. 1, 2005): pp. 7-14: ISSN: 1349-9432.
Zimmerman T et al.: "Spectral Imaging and its Applications in Live Cell Microscopy": FEBS Letters: vol. 546, No. 1: (Jul. 3, 2003): pp. 87-92 ISSN: 0014-5793.
Connah D et al.: "A Computational Model for the Design of a Multispectral Imaging System": Proceedings of IS&T/SID $9^{th}$ Color Imaging Conference (2001): pp. 130-134.
Nakamura K: "Development of Real-Time Endoscopic Image Processing Technology: Adaptive Index of Hemoglobin Color Enhancement Processing": Digestive Endoscopy: vol. 14: (2007): pp. S40-S47.
Garini Y et al: "Spectral Imaging: Principles and Applications": Cytometry Part A: vol. 69A: (2006): pp. 735-747.

\* cited by examiner

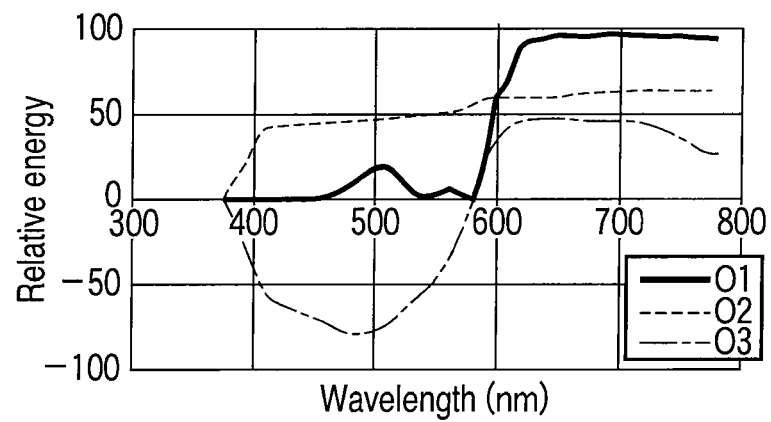
F I G. 7
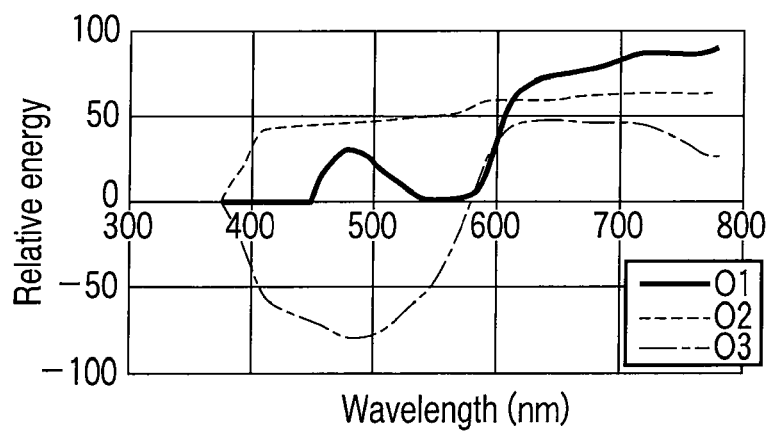
F I G. 8

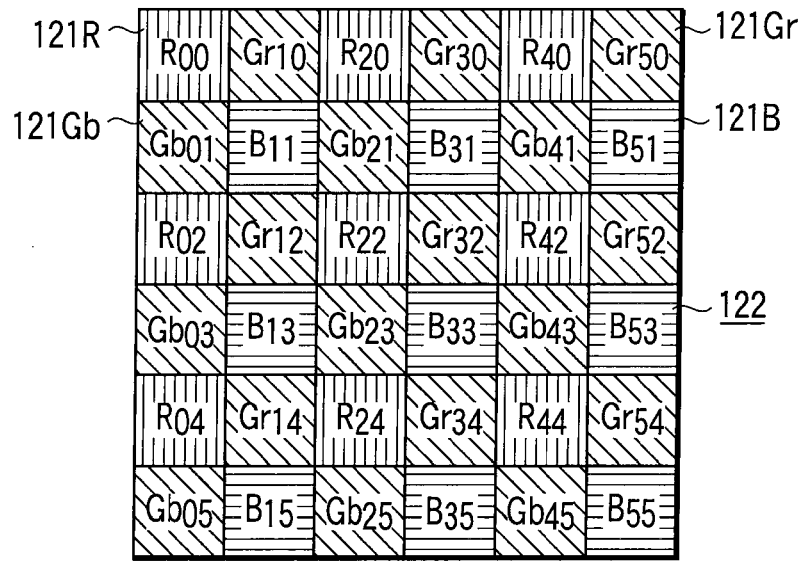
F I G. 9
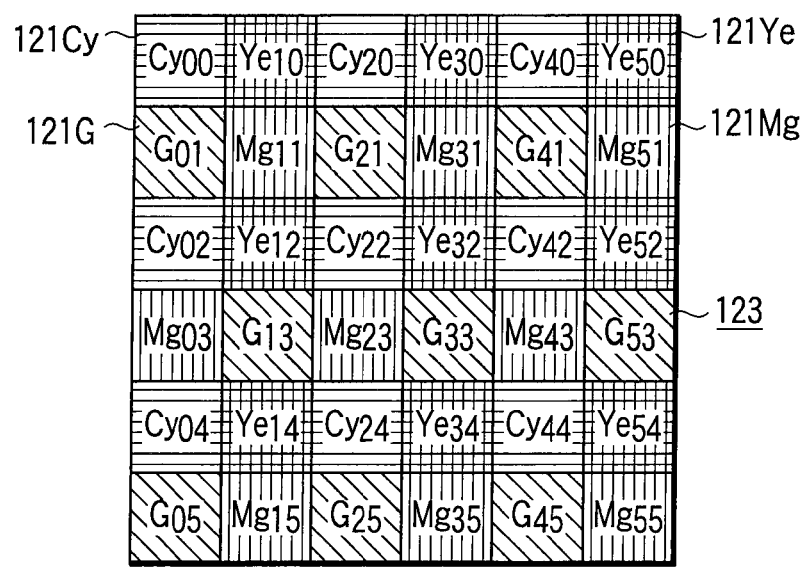
F I G. 10

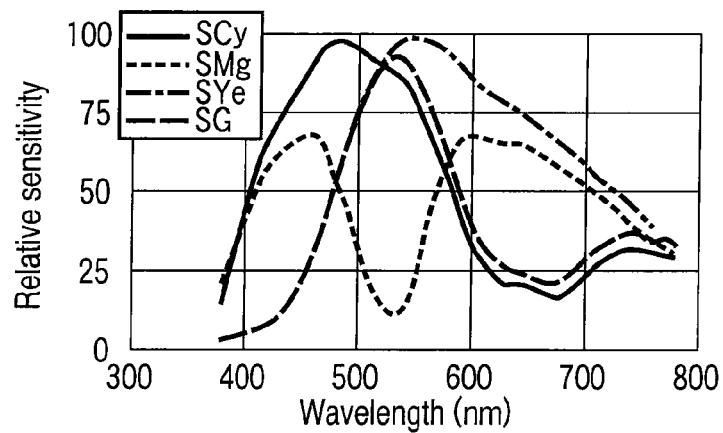
F I G. 11
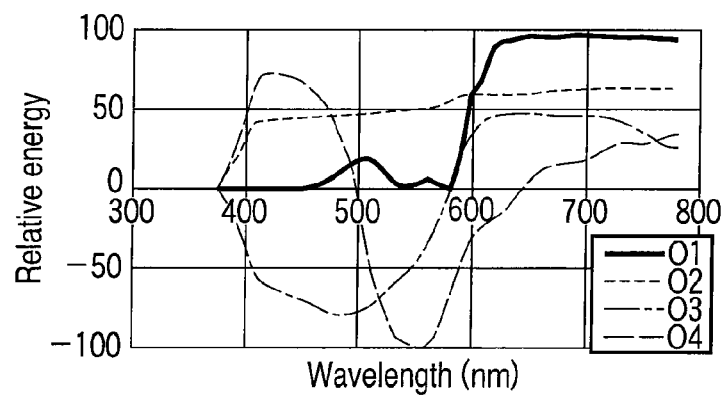
F I G. 12
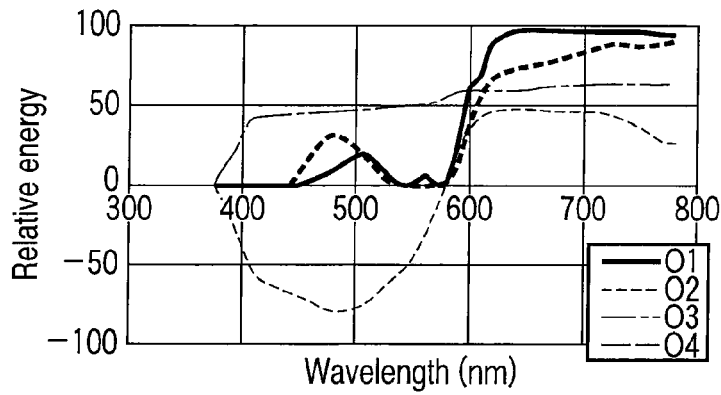
F I G. 13

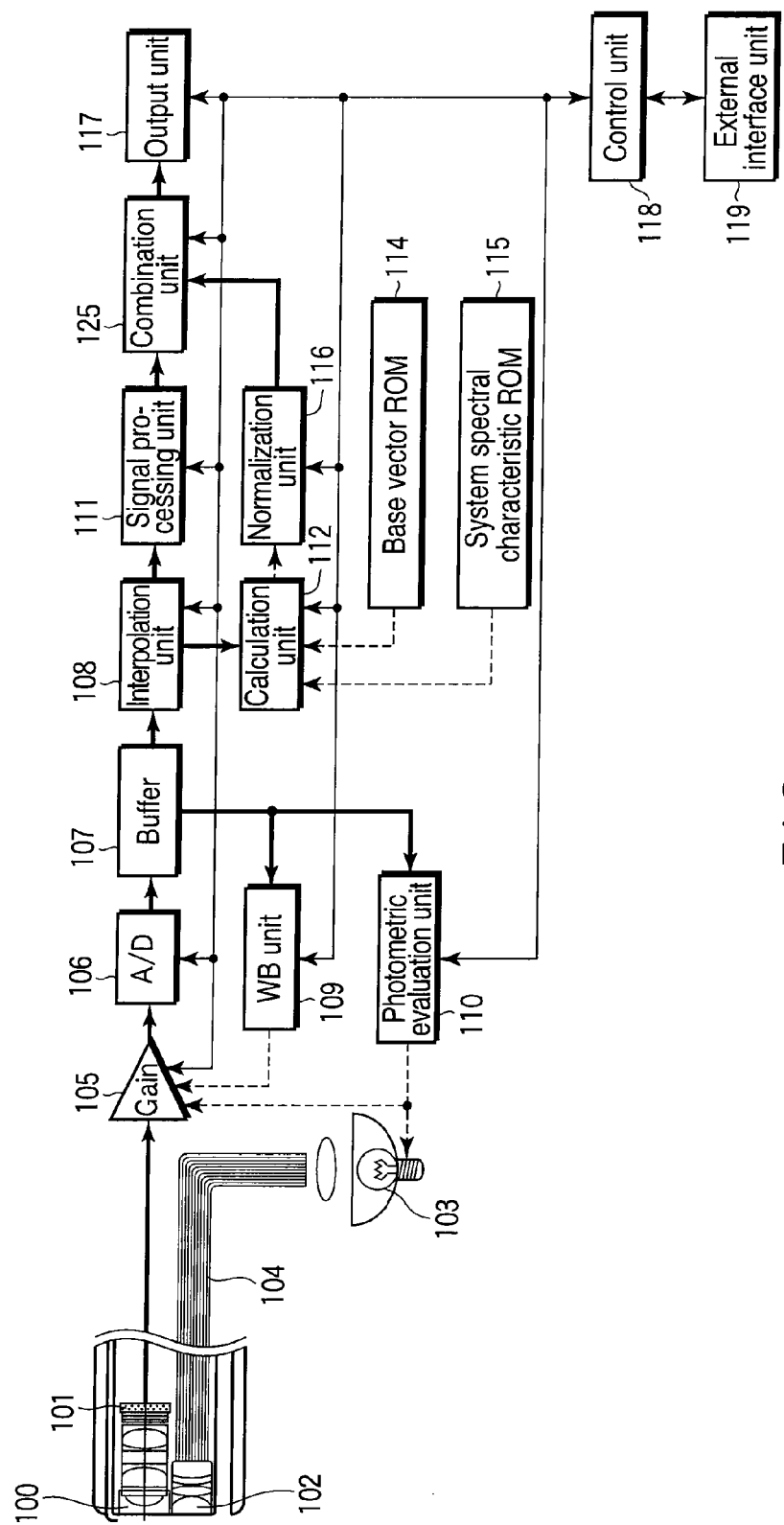
F I G. 15

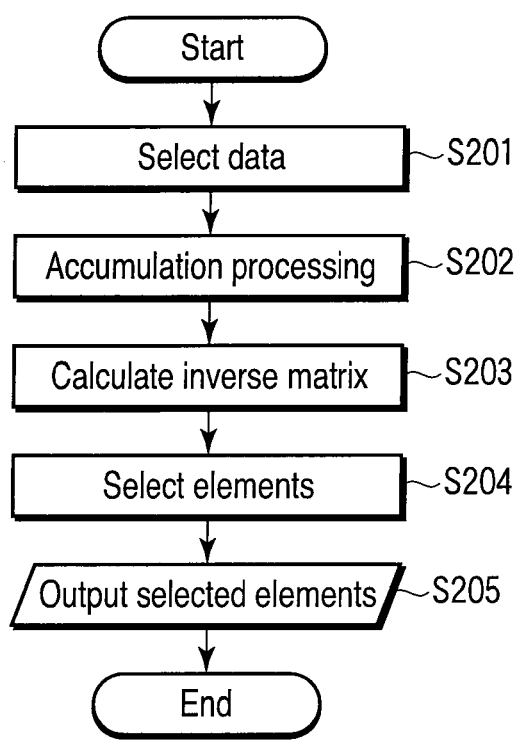
F I G. 19

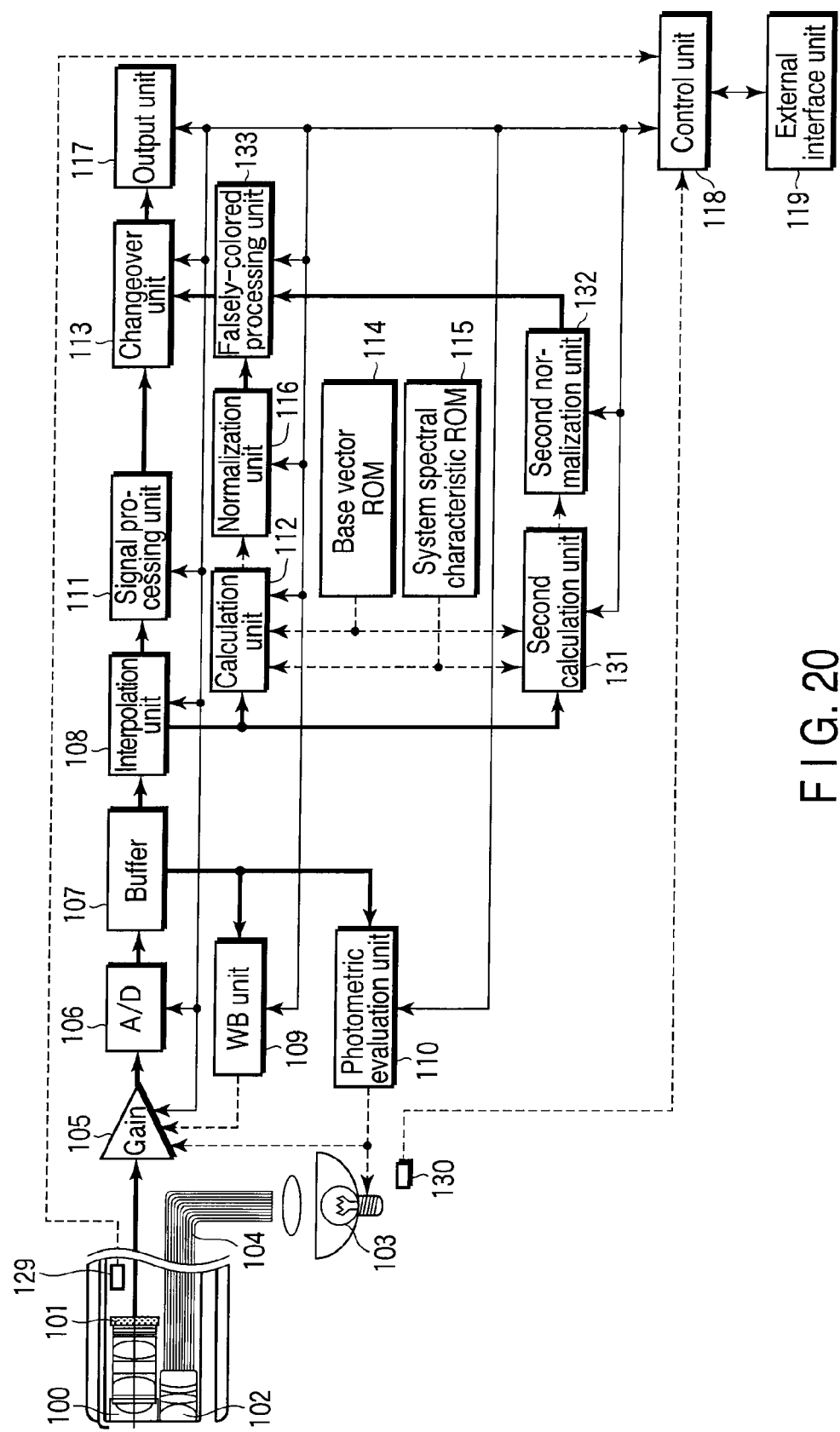
F I G. 20

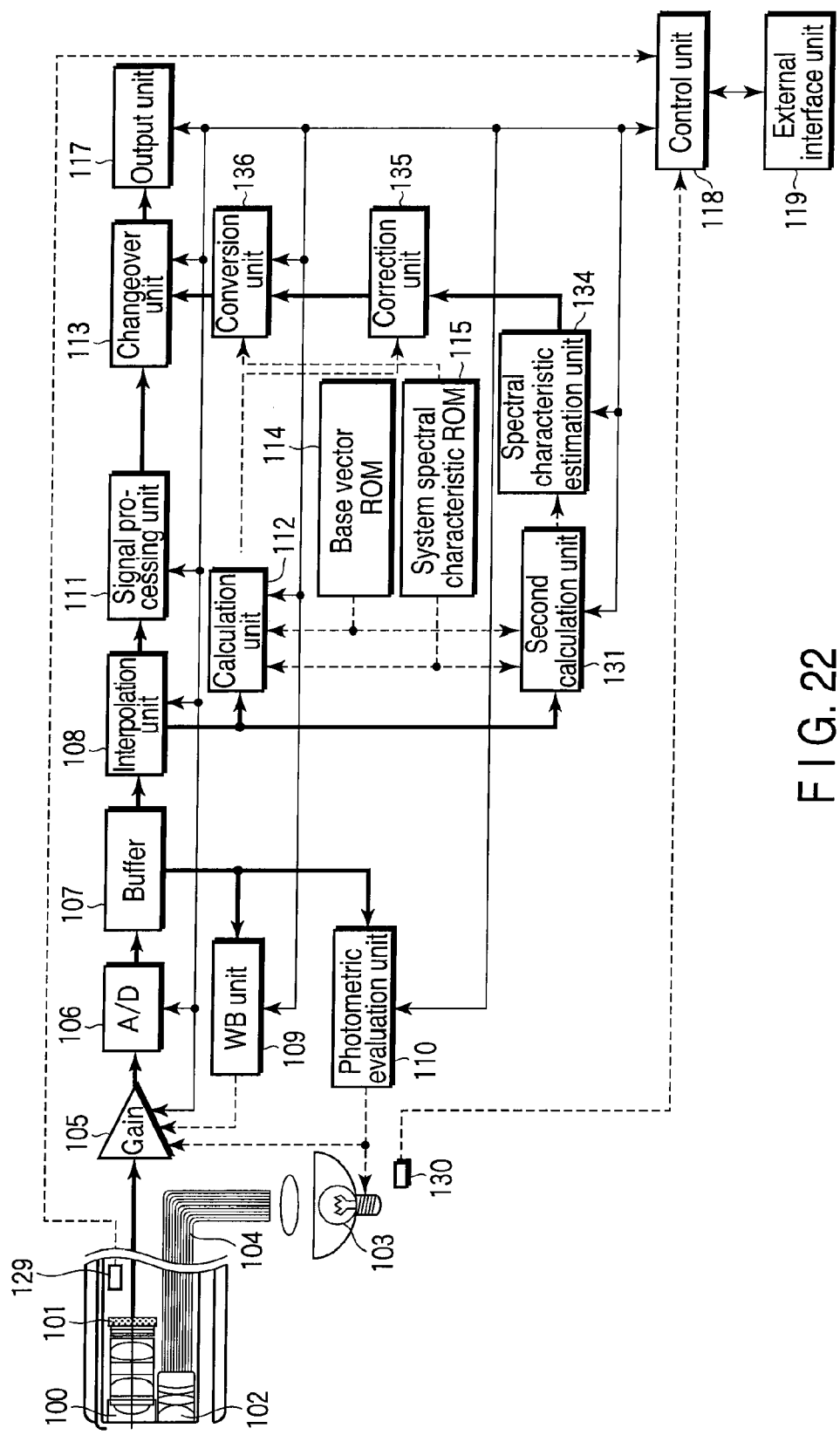
F I G. 22

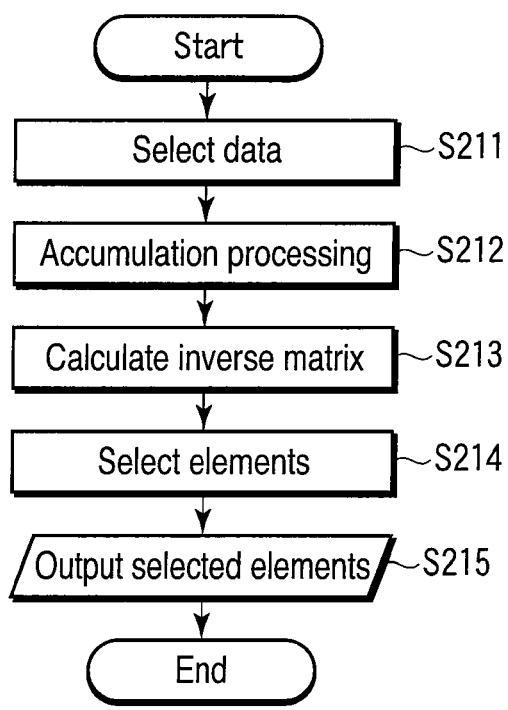
F I G. 25

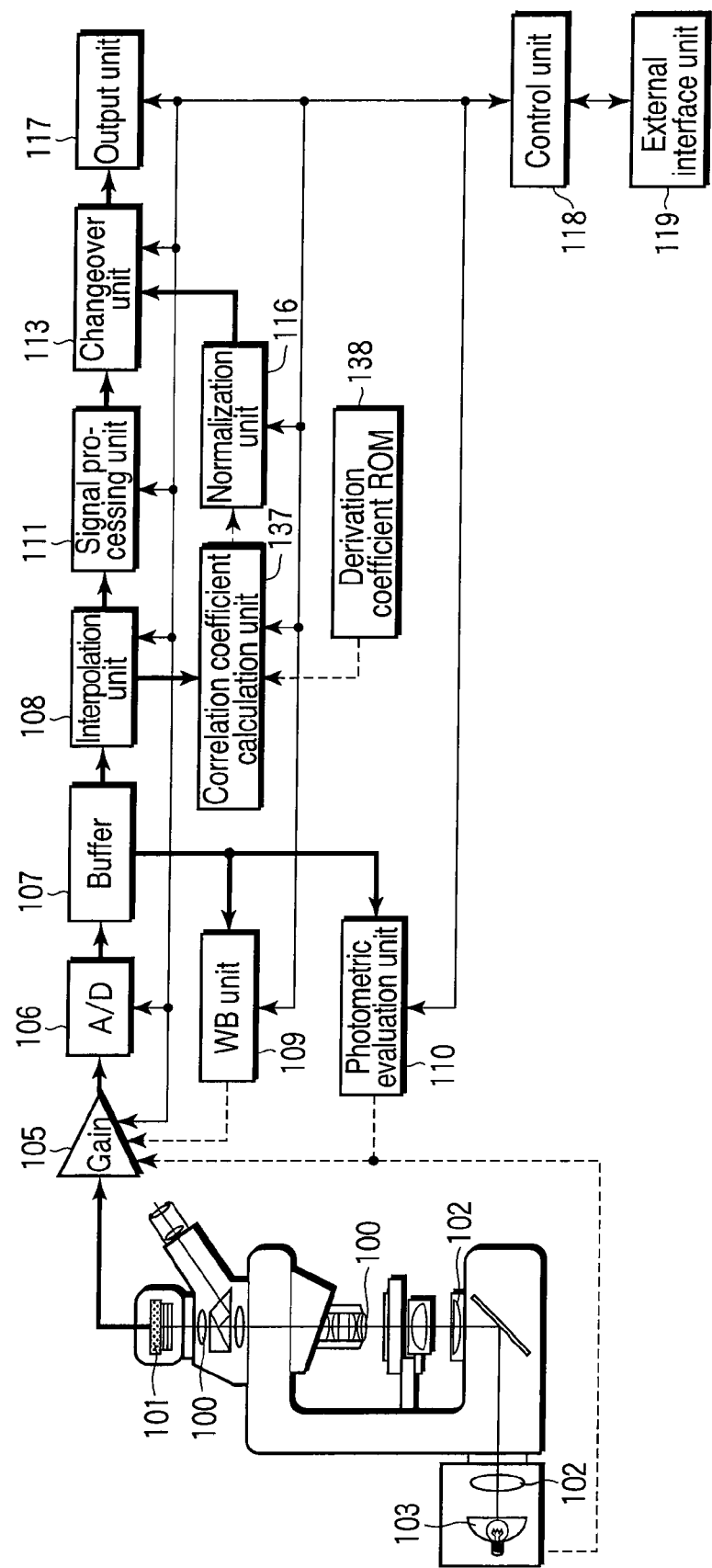
F I G. 26

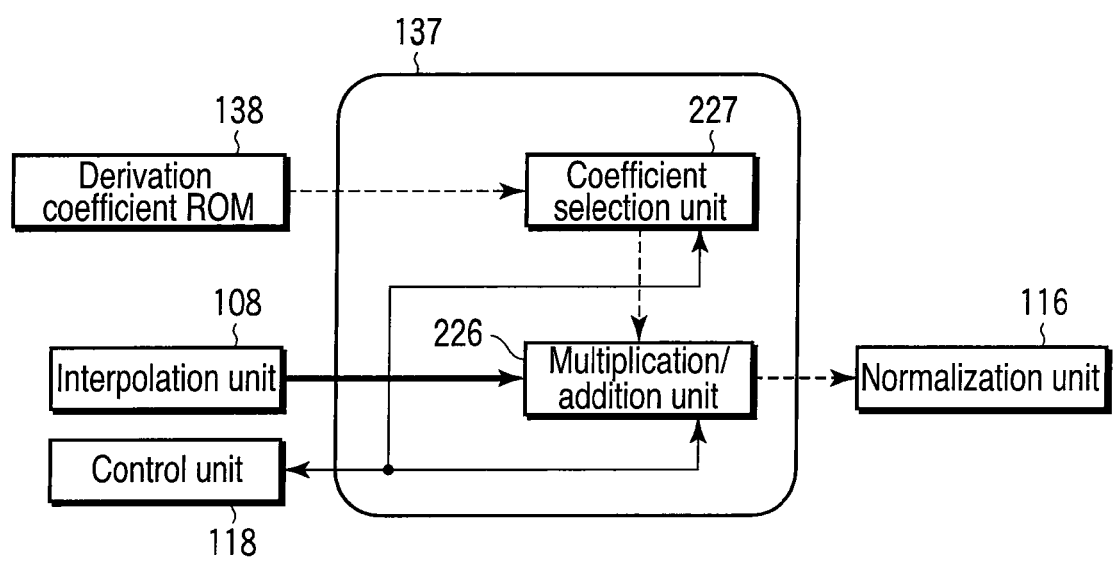
F I G. 27

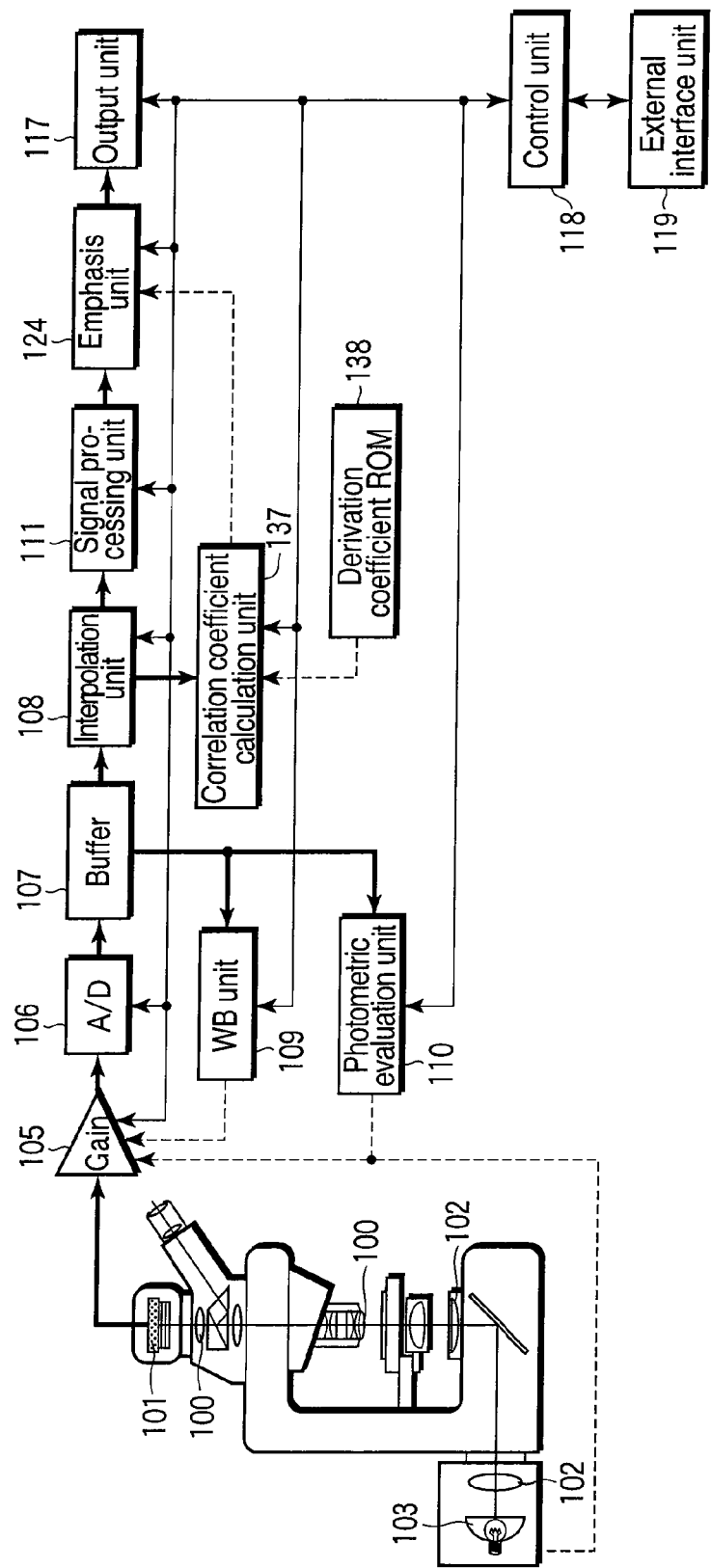
F I G. 28

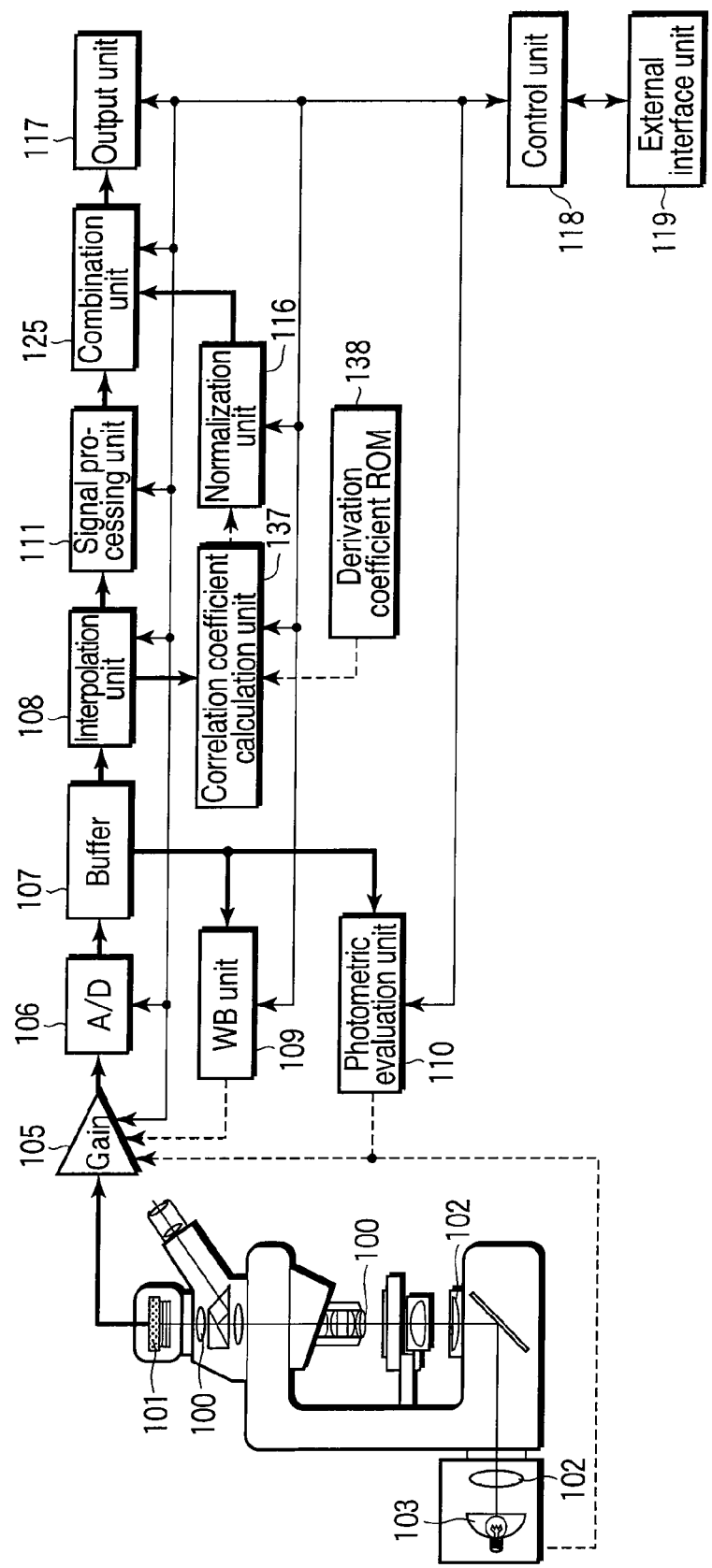
F I G. 29

SIGNAL PROCESSING SYSTEM AND SIGNAL PROCESSING PROGRAM

CROSS REFERENCE TO RELATED APPLICATIONS

This is a Continuation Application of PCT Application No. PCT/JP2009/059551, filed May 25, 2009, which was published under PCT Article 21(2) in Japanese.

This application is based upon and claims the benefit of priority from prior Japanese Patent Application No. 2008-139930, filed May 28, 2008, the entire contents of which are incorporated herein by reference.

BACKGROUND OF THE INVENTION

1. Field of the Invention

The present invention relates to a signal processing system that identifies a subject and a signal processing program that allows a computer to execute a procedure of such a signal processing system.

2. Description of the Related Art

Jpn. Pat. Appln. KOKAI Pub. No. JP-A 2003-93336 discloses an example of using broadband light as observation light to calculate an image signal of a specific narrowband by signal processing. As a result, since a high-quality narrowband image signal with less noise can be obtained, a subject having specific spectral characteristics, e.g., a blood vessel can be identified and output to a display monitor for display, whereby observation of the identification target subject can be facilitated.

BRIEF SUMMARY OF THE INVENTION

According to a first aspect of the present invention, there is provided a signal processing system comprising:

a base vector acquisition unit configured to acquire a dedicated base vector based on a known spectral characteristic of a subject as an identification target;

a system spectral characteristic acquisition unit configured to acquire a spectral characteristic of an imaging system including a spectral characteristic concerning a color imaging system used for image acquisition of subjects including the subject as the identification target and a spectral characteristic concerning illumination light used when image acquisition of the subjects by the color imaging system;

a calculation unit configured to calculate a weighting factor concerning the dedicated base vector based on an image signal obtained by image acquisition of the subject by the color imaging system, the dedicated base vector, and the spectral characteristic of the imaging system; and an output signal calculation unit configured to calculate an output signal as an identification result of the subject which is the identification target based on the weighting factor concerning the dedicated base vector calculated by the calculation unit.

It is to be noted that the acquisition means reading from a recording medium, reading through a network, or the like.

According to a second aspect of the present invention, there is provided a signal processing system comprising:

a derivation coefficient acquisition unit configured to acquire derivation coefficients indicative of a correlation between known spectral characteristic of a subject and an image signal that is calculated based on the known spectral characteristic of the subject as an identification target, spectral characteristic concerning a color imaging system used for image acquisition of subjects including the subject as the identification target, and spectral characteristic concerning illumination light used when image acquisition of subjects by the color imaging system;

a correlation coefficient calculation unit configured to calculate a correlation coefficient between the spectral characteristic of the subject as the identification target and the image signal based on the image signal and the derivation coefficients; and an output signal calculation unit configured to calculate an output signal as an identification result of the subject as the identification target based on the correlation coefficient calculated by the correlation coefficient calculation unit.

According to a third aspect of the present invention, there is provided a signal processing program that allows a computer to:

acquire an image signal obtained by image acquisition of subjects including a subject as an identification target having a known spectral characteristic by a color imaging system;

acquire a dedicated base vector based on the known spectral characteristic of the subject as the identification target;

acquire a spectral characteristic of an imaging system including a spectral characteristic concerning the color imaging system and a spectral characteristic concerning illumination light used for image acquisition of subjects by the color imaging system;

calculate a weighting factor concerning the dedicated base vector based on the acquired image signal, the acquired dedicated base vector, and the acquired spectral characteristic of the imaging system; and calculate an output signal as an identification result of the subject which is the identification target based on the weighting factor concerning the calculated dedicated base vector.

According to a fourth aspect of the present invention, there is provided a signal processing program that allows a computer to:

acquire an image signal obtained by image acquisition of subjects including a subject as an identification target having a know spectral characteristic by a color imaging system;

acquire derivation coefficients indicative of a correlation between the known spectral characteristic of the subject and the image signal that is calculated based on the known spectral characteristic of the subject as the identification target, spectral characteristic of the color imaging system, and spectral characteristic concerning illumination light used for image acquisition of subjects by the color imaging system;

calculate a correlation coefficient between the spectral characteristic of the subject as the identification target and the image signal based on the acquired image signal and the acquired derivation coefficients; and calculate an output signal as an identification result of the subject as the identification target based on the calculated correlation coefficient.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a view showing a dedicated base vector for oxyhemoglobin and two types of general-purpose base vectors as an example of three types of base vectors in Modification 1 of the first embodiment;

FIG. 8 is a view showing a dedicated base vector for deoxyhemoglobin and two types of general-purpose base vectors as an example of the three types of base vectors in Modification 1 of the first embodiment;

FIG. 9 is a view showing a configuration of primary color filters of R, Gr, Gb, and B in Modification 2 of the first embodiment;

FIG. 10 is a view showing a configuration of a color-difference line sequential type complementary filter in Modification 2 of the first embodiment;

FIG. 11 is a view showing spectral sensitivity characteristics of a color imaging system (four complementary colors) in Modification 2 of the first embodiment;

FIG. 12 is a view showing a dedicated base vector for oxyhemoglobin and three types of general-purpose base vectors as an example of four types of base vectors in Modification 2 of the first embodiment;

FIG. 13 is a view showing dedicated base vectors for oxyhemoglobin and deoxyhemoglobin and two types of general-purpose base vectors as an example of four types of base vectors in Modification 2 of the first embodiment;

FIG. 15 is a view showing a configuration of an endoscope to which a signal processing system according to Modification 4 of the first embodiment is applied;

FIG. 19 is a view showing a flowchart concerning calculation processing in FIG. 18;

FIG. 20 is a view showing a configuration of an endoscope to which a signal processing system according to a second embodiment of the present invention is applied;

FIG. 22 is a view showing d configuration of an endoscope to which a signal processing system according to Modification 1 of the second embodiment is applied;

FIG. 25 is a view showing a flowchart concerning second calculation processing in FIG. 24;

FIG. 26 is a view showing a configuration of an microscope to which a signal processing system according to a third embodiment of the present invention is applied;

FIG. 27 is a view showing an example of a configuration of a correlation coefficient calculation unit in FIG. 26;

FIG. 28 is a view showing a configuration of an endoscope to which a signal processing system according to Modification 1 of the third embodiment is applied;

FIG. 29 is a view showing a configuration of an endoscope to which a signal processing system according to Modification 2 of the third embodiment is applied;

DETAILED DESCRIPTION OF THE INVENTION

Modes for carrying out the present invention will now be described hereinafter with reference to the drawings.

First Embodiment

Configuration

Figure 1:
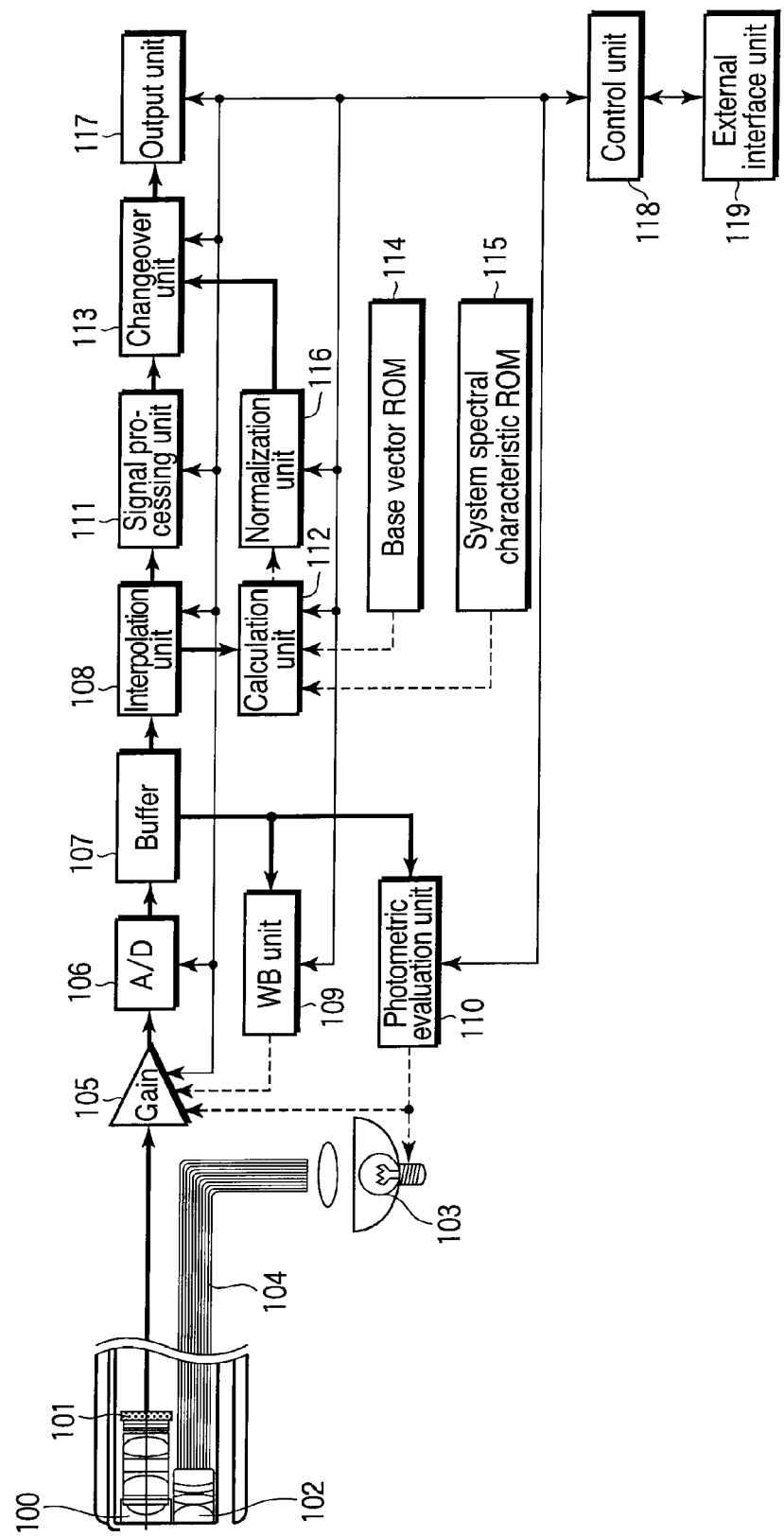
FIG. 1 is a view showing a configuration of an endoscope to which a signal processing system according to a first embodiment of the present invention is applied.

As shown in FIG. 1, an endoscope to which a signal processing system according to a first embodiment of the present invention is applied includes an imaging lens system 100, a CCD 101, an illumination lens system 102, an illumination light source 103, an optical fiber 104, an amplification unit (which is represented as Gain in the drawing) 105, an analog-to-digital converter (which is represented as A/D in the drawing) 106, a buffer 107, an interpolation unit 108, a WB unit 109, a photometric evaluation unit 110, a signal processing unit 111, a calculation unit 112, a changeover unit 113, a base vector ROM 114, a system spectral characteristic ROM 115, a normalization unit 116, an output unit 117, a control unit 118, and an external interface unit 119. It is to be noted that each arrow of a heavy solid line indicates a direction of an image signal, each arrow of a narrow solid line indicates a direction of a control signal, and each arrow of a broken line indicates a direction of any other signal (such indication is likewise applied to other drawings).

The imaging lens system 100, the COD 101, and the illumination lens system 102 are arranged at a distal portion of the endoscope that is inserted into a body of a patient. The illumination light source 103 is arranged on, e.g., an endoscope rear end side, and illumination light from the illumination light source, 103 is led to the endoscope distal portion through the optical fiber 104 and applied to a non-illustrated subject through the illumination lens system 102. The COD 101 acquires an image of the thus illuminated subjected, and an image signal obtained by this image acquisition is amplified by the amplification unit 105, and then converted into a digital signal by the analog-to-digital converter 106.

The digital image signal from the analog-to-digital converter 106 is transferred to the interpolation unit 108 via the buffer 107. Further, the buffer 107 is also connected to the WB unit 109 and the photometric evaluation unit 110. The WE unit 109 is connected to the amplification unit 105, and the photometric evaluation unit 110 is connected to the illumination light source 103 and the amplification unit 105. The interpolation unit 108 is connected to the signal processing unit 111 and the calculation unit 112. The signal processing unit 111 is connected to the changeover unit 113.

The base vector ROM 114 and the system spectral characteristic ROM 115 are connected to the calculation unit 112. The calculation unit 112 is connected to the changeover unit 113 via the normalization unit 116. The changeover unit 113 is connected to the output unit 117 such as a liquid crystal display.

The control unit 118 such as a microcomputer is bi-directionally connected with the amplification unit 105, the analog-to-digital converter 106, the interpolation unit 108, the WE unit 109, the photometric evaluation unit 110, the signal processing unit 111, the calculation unit 112, the changeover unit 113, the normalization unit 116, and the output unit 117. Further, the external interface unit 119 including a power supply switch, a shutter button, and an interface configured to switch various modes at the time of image acquisition is also bi-directionally connected with this control unit 118.

(Function)

Flows of signals will now be explained with reference to FIG. 1.

After an image acquisition condition such as a subject to be an identification target, the color imaging system, the illumination light, and the like which are described later, have been set through the external interface unit 119, the endoscope is entered an image acquisition mode by pressing the shutter button. As described above, the external interface unit 119 functions as, e.g., an identification target selection unit that selects one subject from a plurality of subjects as identification targets and a color imaging system selection unit that selects one color imaging system and one illumination light from a plurality of color imaging systems and a plurality of illumination lights.

In this image acquisition mode, image signals obtained by image acquisition using the CCD 101 are continuously output from the COD 101 at predetermined time intervals as analog signals. In the following description, a plurality of image signals that are continuously output will be simply referred to as an image signal, the image signal corresponding to one image will be referred to as a frame signal. Furthermore, in this embodiment, 1/30 second (which will be referred to as one frame time hereinafter) is assumed as the predetermined time interval.

Figure 2:
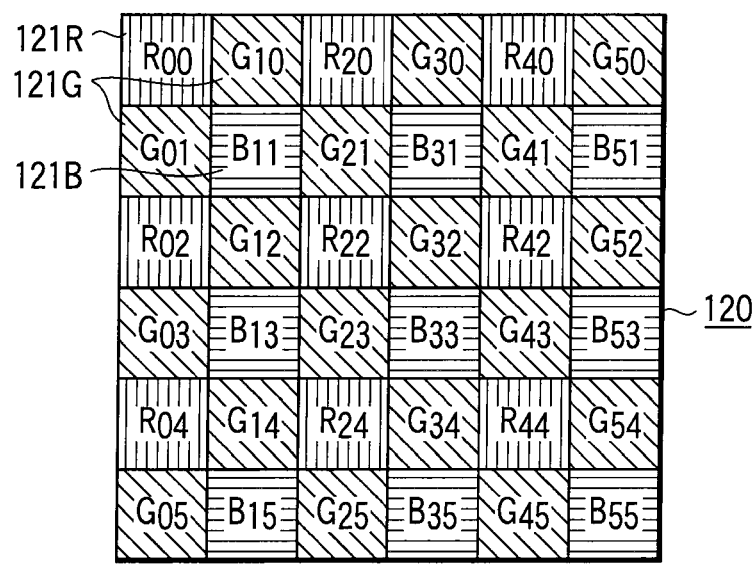
FIG. 2 is a view showing a configuration of a Bayer type primary color filter.

Moreover, as the COD 101, a single COD having such a Bayer type primary color filter 120 as shown in FIG. 2 arranged on a front surface thereof is assumed. In the Bayer type, a basic unit is 2×2 pixels, and each of a red (R) color filter 121R and a blue (B) color filter 121B is arranged for one pixel and green (B) color filters 121G are arranged for two pixels in the basic unit.

The analog signals from the CCD 101 are amplified by a predetermined amount in the amplification unit 105, converted into digital signals by the analog-to-digital converter 106, and transferred to the buffer 107. This buffer 107 can record signals for one frame, and overwriting is sequentially performed from older frame signal as image acquisition advances. Each frame signal in this buffer 107 is intermittently transferred to the WB unit 109 and the photometric evaluation unit 110 at the predetermined time intervals under control of the control unit 118.

In the WB unit 109, white balance coefficients are calculated by integrating signals on a predetermined level, e.g., an intermediate level in accordance with each color signal associated with the color filter 121R, 121G, or 121B. Additionally, the calculated white balance coefficients are transferred to the amplification unit 105. The amplification unit 105 performs white balance adjustment by multiplying the white balance coefficient that differs depending on each color signal by a gain. Further, the photometric evaluation unit 110 controls a light amount of the illumination light source 103 or a gain of the amplification unit 105 to obtain appropriate exposure.

On the other hand, the interpolation unit 108 reads the Bayer type single CCD signal from the buffer 107 under control of the control unit 118 and generates three color frame signal by known interpolation processing. The generated three color frame signal is sequentially transferred to the signal processing unit 111 and the calculation unit 112 in units of frame signal. The signal processing unit 111, the calculation unit 112, and the normalization unit 116 on subsequent stages execute processing in synchronization with each other in units of three color frame signal under control of the control unit 118.

The signal processing unit 111 executes known gradation processing and emphasis processing with respect to frame signal transferred from the interpolation unit 108 and transfers the processed frame signal to the changeover unit 113 under control of the control unit 118.

On the other hand, the base vector ROM 114 stores a dedicated base vector based on a known spectral characteristic of each of a plurality of subjects as identification targets. Furthermore, the system spectral characteristic ROM 115 stores a spectral characteristic concerning each of the plurality of color imaging systems and a spectral characteristic concerning each of the plurality of illumination lights used at the time of image acquisition. It is to be noted that the spectral characteristic concerning the color imaging system means spectral sensitivity characteristics of the CCD 101 having a tinge of a spectral transmittance characteristic of the imaging lens system 100 added thereto. Further, the spectral characteristic concerning the illumination light means a spectral luminance characteristic of the illumination light source 103 having a tinge of a spectral transmittance characteristic of the transfer optical fiber 104 and the illumination lens system 102 added thereto.

The calculation unit 112 reads base vectors from the base vector ROM 114 and a spectral characteristic from the system spectral characteristic ROM 115, respectively, based on control of the control unit 118 meeting the image acquisition condition set through the external interface unit 119. That is, a dedicated base vector based on a known spectral characteristic of one subject as an identification target and dedicated base vectors based on known spectral characteristics of non-identification-target subjects are read from the base vector ROM 114. Furthermore, spectral characteristic of the imaging system including a spectral characteristic concerning one color imaging system used for image acquisition of subjects including the one subject as the identification target and a spectral characteristic concerning one illumination light used at the time of image acquisition of the subjects by this color imaging system are read from the system spectral characteristic ROM. Then, as will be described later, the calculation unit 112 utilizes the dedicated base vectors, the spectral characteristic concerning the color imaging system, and the spectral characteristic concerning the illumination light, which have been read out, with respect to the frame signal transferred from the interpolation unit 108 to calculate a weighting factor concerning the dedicated base vector of the subject as the identification target. The calculated weighting factor of the dedicated base vector takes a value that is proportionate to presence of the subject as the identification as will be described later, and it is transferred to the normalization unit 116. The normalization unit 116 executes normalization processing with respect to the weighting factor transferred from the calculation unit 112 under control of the control unit 118 in such a manner that the weighting factor coincides with a signal level of the image signal. That is, since the weighting factor calculated by the calculation unit 12 takes a value of "0" to "1", it is normalized to a value of "0" to "255" if the signal level consists of 8 bits. Moreover, the normalized weighting factor is transferred as a frame signal to the changeover unit 113.

The changeover unit 113 selects either the ordinary frame signal transferred from the signal processing unit 111 or the frame signal that is transferred from the normalization unit 116 and concerns presence of an identification target under control of the control unit 118. The selected frame signal is transferred to the output unit 117 to be output. In this manner, the changeover unit 113, the normalization unit 116, and the output unit 117 function as an output signal calculation unit that calculates an output signal which is an identification result of the subject as the identification target based on the weighting factor concerning the dedicated base vector, for example. It is to be noted that the frame signal from the normalization unit 116 is output as a monochrome signal. For example, if the output unit 117 is a display monitor, the transferred frame signal is displayed. The output unit 117 is not restricted to the display monitor, and it can take a conformation that sequentially records and stores frame signals in a recording medium such as a hard disk or a memory card.

Figure 3:
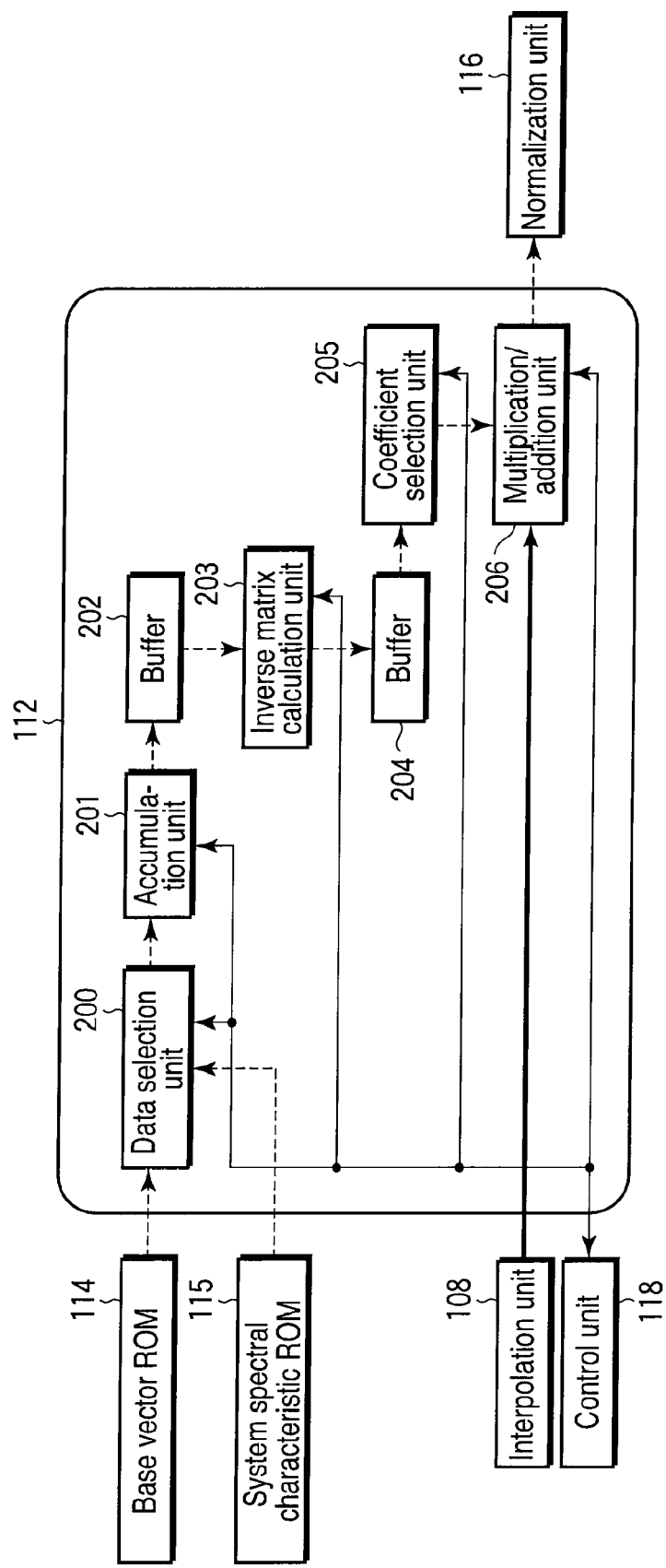
FIG. 3 is a view showing an example of a configuration of a calculation unit in FIG. 1.

As shown in FIG. 3, the calculation unit 112 is constituted of a data selection unit 200, an accumulation unit 201, a buffer 202, an inverse matrix calculation unit 203, a buffer 204, a coefficient selection unit 205, and a multiplication/addition unit 206. The base vector ROM 114 and the system spectral characteristic ROM 115 are connected to the data selection unit 200. The data selection unit 200 is connected to the coefficient selection unit 205 via the accumulation unit 201, the buffer 202, the inverse matrix calculation unit 203, and the buffer 204. The coefficient selection unit 205 and the interpolation unit 108 are connected to the multiplication/addition unit 206. The multiplication/addition unit 206 is connected to the normalization unit 116. The control unit 118 is bi-directionally connected to the data selection unit 200, the accumulation unit 201, the inverse matrix calculation unit 203, the coefficient selection unit 205, and the multiplication/addition unit 206.

The data selection unit 200 receives from the control unit 118 information of a subject as an identification target under the image acquisition condition set through the external interface unit 119. Further, based on this information, this unit reads a plurality of dedicated base vectors including a dedicated base vector based on known spectral characteristic of the subject as the identification target from the base vector ROM 114. In this manner, the base vector ROM 114 and the data selection unit 200 function as a base vector acquisition unit that acquires the dedicated bas vector based on the known spectral characteristic of the subject as the identification target, for example. In this embodiment, since the Bayer type including the three color filters 121R, 121G, and 121B is assumed as the COD 101, a total number of dedicated base vectors is three. As one of the three types of dedicated base vectors, a dedicated base vector based on the known spectral characteristic of the set subject as the identification target is used.

Figure 4:
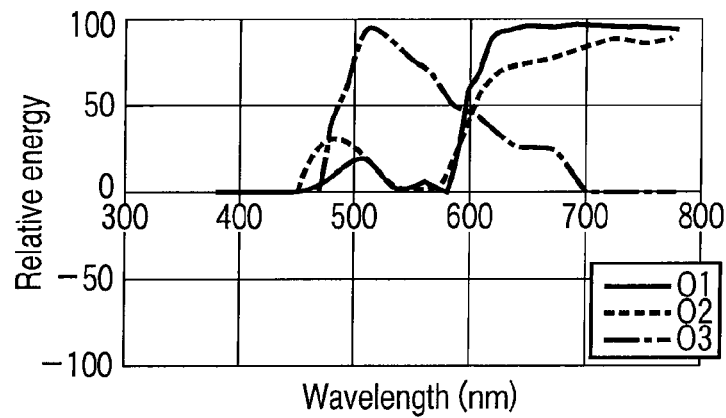
FIG. 4 is a view showing an example of three types of dedicated base vectors.

FIG. 4 shows three types of dedicated base vectors ($O1(\lambda)$, $O2(\lambda)$, $O3(\lambda)$) as examples of the dedicated base vectors. It is to be noted that $\lambda$, means, e.g., a visible range of a wavelength of 380 to 780 nm. In FIG. 4, the dedicated base vector ($O1(\lambda)$) is based on spectral reflectance characteristic of oxyhemoglobin, and the dedicated base vector ($O2(\lambda)$) is based on a spectral reflectance characteristic of deoxyhemoglobin. Since large amounts of oxyhemoglobin and deoxyhemoglobin are contained in a vascular region, they are important in a diagnosis using an endoscope. Further, the dedicated base vector ($O3(\lambda)$) is based on a spectral luminance characteristic of auto-fluorescence of collagen which is a primary subject in fluorescent observation.

An abundance of oxyhemoglobin is contained in an artery, and an abundance of deoxyhemoglobin is contained in a vein. Thus, when observing, e.g., an artery, the oxyhemoglobin is specified as a subject which is an identification target, through the external interface unit 119. As a result, the data selection unit 200 reads the three dedicated base vectors including at least the oxyhemoglobin dedicated base vector ($O1(\lambda)$). Each of the other two dedicated base vectors is a dedicated base vector of a subject which is not an identification target, and these vectors may be, e.g., the deoxyhemoglobin dedicated base vector ($O2(\lambda)$) and the collagen dedicated base vector ($O3(\lambda)$) or other dedicated base vectors stored in the base vector ROM 114.

A description will now be given on the assumption that the oxyhemoglobin is specified as a subject which is an identification target.

The data selection unit 200 further receives from the control unit 118 information of the color imaging system and illumination light under the image acquisition condition set through the external interface unit 119. Additionally, it reads from the system spectral characteristic ROM 115 a spectral characteristic of the imaging system including a spectral characteristic concerning the color imaging system used for image acquisition of subjects and a spectral characteristic concerning the illumination light used at the time of image acquisition of the subjects by using the color imaging system. In this manner, the system spectral characteristic ROM 115 and the data selection unit 200 function as a system spectral characteristic acquisition unit that acquires spectral characteristic of the imaging system, for example.

Figure 5:
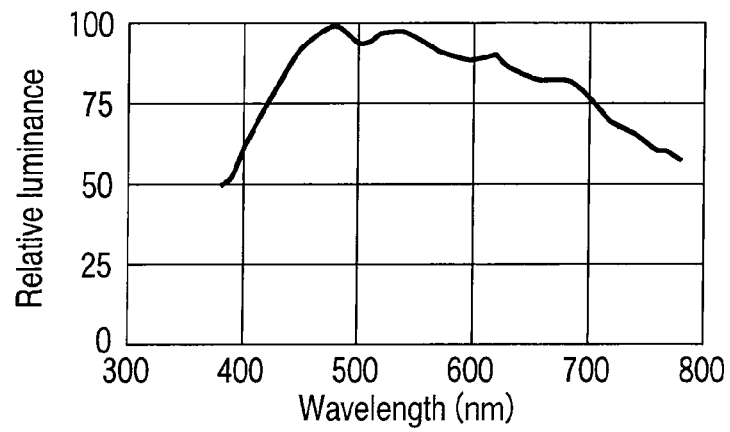
FIG. 5 is a view showing an example of a spectral luminance characteristic of a light source as spectral characteristics concerning illumination light used at the time of image acquisition.
Figure 6:
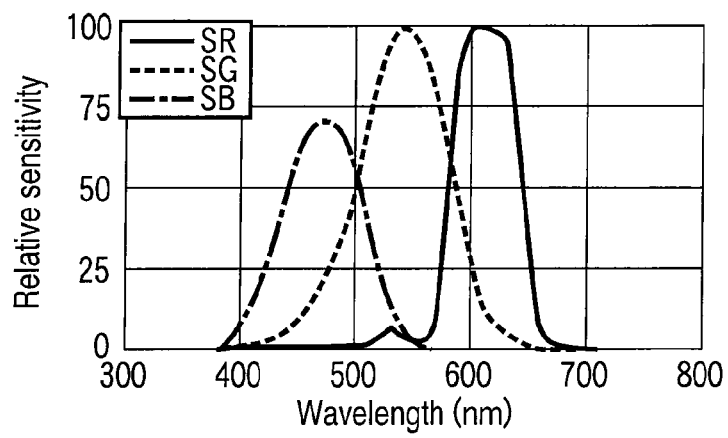
FIG. 6 is a view showing an example of spectral sensitivity characteristics of a color imaging system including color filters of R, G, and B as a spectral characteristic concerning the color imaging system.
Figure 14:
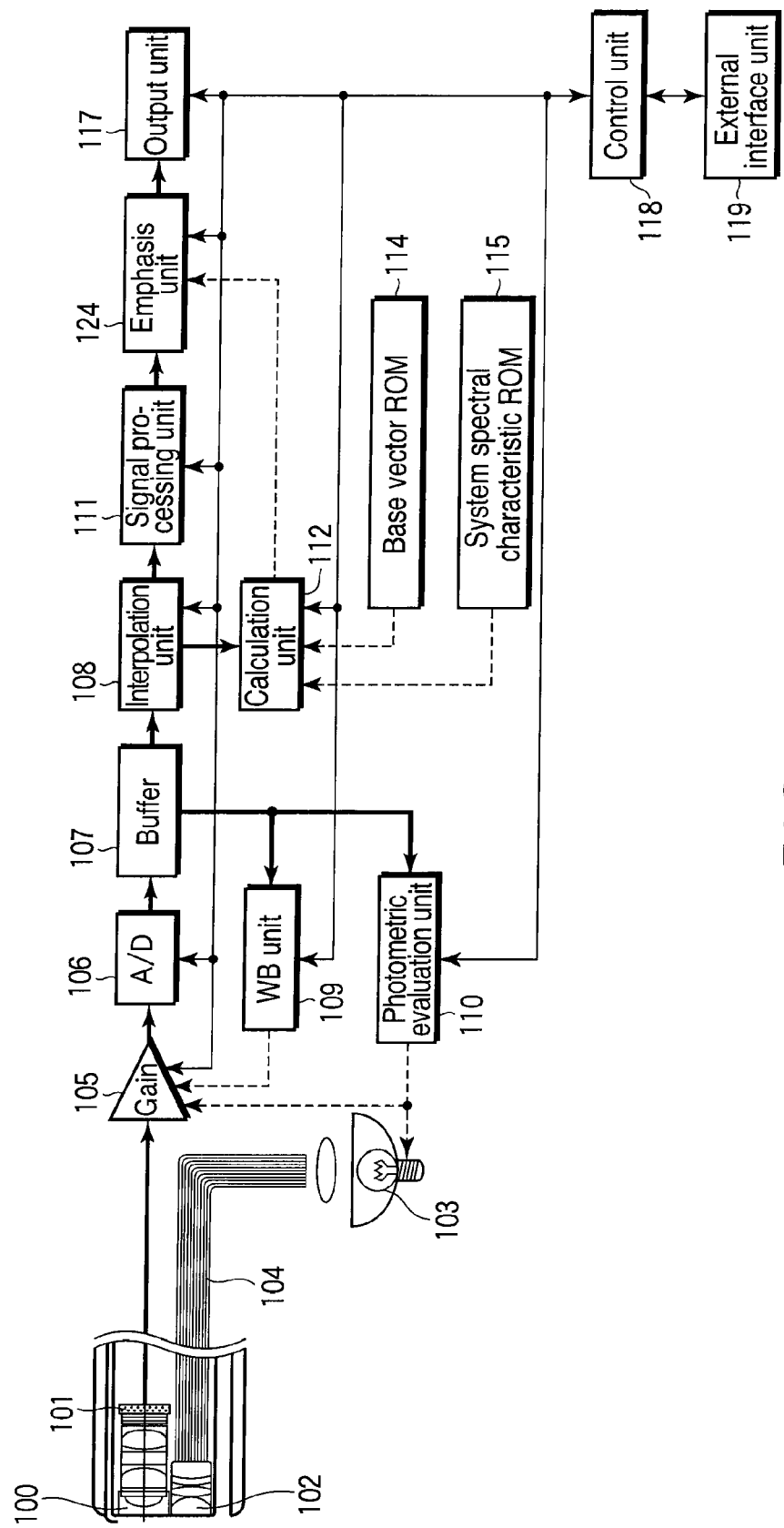
FIG. 14 is a view showing a configuration of an endoscope to which a signal processing system according to Modification 3 of the first embodiment is applied.

FIG. 5 shows a spectral luminance characteristic ($I(\lambda)$) of a xenon light source as an example of the spectral characteristic concerning the illumination light used at the time of image acquisition of the subjects. Furthermore, FIG. 6 shows spectral sensitivity characteristics ($SR(\lambda)$ $SG(\lambda)$, $SB(\lambda)$) of the color imaging system including the three color filters 121R, 121G, and 121B of R, G, and B as an example of the spectral characteristic of the color imaging system.

The data selection unit 200 transfers the read dedicated base vectors ($O1(\lambda)$, $O2(\lambda)$, $O3(\lambda)$), a spectral luminance characteristic ($I(\lambda)$) of the light source, and spectral sensitivity characteristics ($SR(\lambda)$, $SG(\lambda)$, $SB(\lambda)$) of the color imaging system to the accumulation unit 201.

The accumulation unit 201 calculates a system matrix M concerning the imaging system of a 3×3 size represented by the following expression (1) under control of the control unit 118.

$$M = \begin{bmatrix} \sum_{\lambda=380,780} I(\lambda) \cdot SR(\lambda) \cdot O1(\lambda) & \sum_{\lambda=380,780} I(\lambda) \cdot SR(\lambda) \cdot O2(\lambda) & \sum_{\lambda=380,780} I(\lambda) \cdot SR(\lambda) \cdot O3(\lambda) \\ \sum_{\lambda=380,780} I(\lambda) \cdot SG(\lambda) \cdot O1(\lambda) & \sum_{\lambda=380,780} I(\lambda) \cdot SG(\lambda) \cdot O2(\lambda) & \sum_{\lambda=380,780} I(\lambda) \cdot SG(\lambda) \cdot O3(\lambda) \\ \sum_{\lambda=380,780} I(\lambda) \cdot SR(\lambda) \cdot O1(\lambda) & \sum_{\lambda=380,780} I(\lambda) \cdot SB(\lambda) \cdot O2(\lambda) & \sum_{\lambda=380,780} I(\lambda) \cdot SB(\lambda) \cdot O3(\lambda) \end{bmatrix} \quad (1)$$

In this manner, the data selection unit 200 and the accumulation unit 201 function as a matrix calculation unit that calculates a system matrix concerning the imaging system, for example.

The system matrix M calculated by this accumulation unit 201 is transferred to and stored in the buffer 202. The inverse matrix calculation unit 203 reads the system matrix M from this buffer 202 and calculates an inverse matrix $M^{-1}$ of the system matrix M under control of the control unit 118. The calculated inverse matrix $M^{-1}$ is transferred to and stored in the buffer 204.

Weighting factors (w1, w2, w3) concerning the dedicated base vectors (O1(λ), O2(λ), O3(λ)) in units of each pixel can be obtained based on the following expression (2) by using the inverse matrix $M^{-1}$ of the system matrix M and frame signal consisting of R, G, and B. It is to be noted that, in the following expression (2), i and j mean a coordinate in x and y directions of frame signal and m means each element of the inverse matrix $M^{-1}$ of the system matrix M, i.e., a coefficient of the inverse matrix $M^{-1}$.

$$\begin{bmatrix} w1_{ij} \\ w2_{ij} \\ w3_{ij} \end{bmatrix} = M^{-1} \begin{bmatrix} R_{ij} \\ G_{ij} \\ B_{ij} \end{bmatrix} = \begin{bmatrix} m_{11} & m_{12} & m_{13} \\ m_{21} & m_{22} & m_{23} \\ m_{31} & m_{32} & m_{33} \end{bmatrix} \begin{bmatrix} R_{ij} \\ G_{ij} \\ B_{ij} \end{bmatrix} \quad (2)$$

In this embodiment, since the oxyhemoglobin voluminously contained in a vessel region that is important in a diagnosis using an endoscope is assumed to be an identification target, obtaining a weighting factor ($w1_{ij}$) concerning the dedicated base vector (O1(λ)) of the subject as the identification target can suffice. Therefore, required coefficients of the inverse matrix $M^{-1}$ of the system matrix M are three elements $m_{11}$, $m_{12}$, and $m_{13}$.

Thus, the coefficient selection unit 205 selects the elements $m_{11}$, $m_{12}$, and $m_{13}$ of the inverse matrix $M^{-1}$ of the system matrix M from the buffer under 204 under control of the control unit 118, and transfers them to the multiplication/addition unit 206. After transfer of the elements $m_{11}$, $m_{12}$, and $m_{13}$ of the inverse matrix $M^{-1}$ of the system matrix M from the coefficient selection unit 205, the multiplication/addition unit 206 reads frame signal from the interpolation unit 109 in units of pixels consisting of R, C, and B under control of the control unit 118. Further, the multiplication/addition unit 206 obtains the weighting factor ($w1_{ij}$) concerning the dedicated base vector (O1(λ)) of the subject as the identification target based on the following expression (3).

$$w1_{ij} = m_{11} \cdot R_{ij} + m_{12} \cdot G_{ij} + m_{13} \cdot B_{ij} \quad (3)$$

Since the weighting factor ($w1_{ij}$) serves as a contribution degree with respect to the dedicated base vector (O1(λ)) of the subject as the identification target, it takes a value that is proportionate to presence of the oxyhemoglobin in this embodiment. That is, it takes a high value when the oxyhemoglobin is present, and it takes a low value when the same is not present. Therefore, converting this weighting factor ($w1_{ij}$) into an image signal enables identifying the oxyhemoglobin.

Thus, the weighting factor ($w1_{ij}$) calculated by the multiplication/addition unit 206 is sequentially transferred to the normalization unit 116 to be normalized as described above. Furthermore, the normalized weighting factor is transferred to and displayed in the output unit 117 which is, e.g., a display monitor through the changeover unit 113 as an output signal that is an identification result of the subject having the known spectral characteristics.

It is to be noted that the identification target is the oxyhemoglobin in the above description, but it is not of course restricted thereto. For example, the subject as the identification target may be changed over to the deoxyhemoglobin through the external interface unit 119 as required.

Moreover, a configuration that obtains weighting factors ($w1_{ij}$, $w2_{ij}$) of both the oxyhemoglobin and the deoxyhemoglobin may be adopted. In this case, the plurality of multiplication/addition units 206 may be provided, or a combination of one multiplication/addition unit 206 and a buffer that stores the calculated weighting factors may be used as the configuration. Additionally, in regard to a method of outputting a calculation result of the two weighting factors, a configuration that selects each factor through the external interface unit 119 and displays the selected one, a configuration that combines and displays both the factors, or a configuration that falsely-colored processes both the factors and independently displays them can be freely set.

As described above, according to the first embodiment, the weighting factor concerning the dedicated base vector that takes a value proportional to presence of the subject as the identification target is calculated from the dedicated base vector based on a known spectral characteristic of the subject as the identification target, the spectral characteristic concerning the color imaging system used for image acquisition of subjects including the subject as the identification target, and the spectral characteristic concerning illumination light used for image acquisition of subjects by the color imaging system, and an output signal as an identification result of the subject which is the identification target is calculated based on this weighting factor. As described above, in the first embodiment, the weighting factor that takes a value that is proportionate to presence of the subject as the identification target can be calculated by using the dedicated base vector based on the known spectral characteristic of the subject as the identification target. Therefore, signal processing containing an error like approximation based on the conventional least-square method does not have to be executed. Accordingly, an error due to the signal processing hardly occurs, and the subject as the identification target can be identified with high reliability.

Additionally, since the ordinary broadband illumination light is used, an influence of noise can be suppressed, and stable identification can be carried out.

Further, since the output signal is directly calculated from the weighting factor concerning the dedicated base vector, an increase in speed of processing and a reduction in cost can be achieved.

Furthermore, as the dedicated base vectors, the dedicated base vector based on the known spectral characteristic of the subject as the identification target and the dedicated base vectors based on the known spectral characteristics of the non-identification-target subjects which have the known spectral characteristics but are not the identification target are used. Therefore, signal processing using the dedicated base vectors can be applied to a region which is not the identification target, and a freedom degree in the subsequent processing of calculating an output signal can be improved.

Moreover, a choice of the subject as the identification target is accepted, and the dedicated base vector of the subject as the identification target is selected from a plurality of dedicated base vectors in accordance with this choice. Therefore, the subject as the identification target can be selected, applicability as the system can be improved, thereby enabling utilization for various purposes.

Additionally, choices of the color imaging system and the illumination light are accepted, and spectral characteristics to be used are selected from spectral characteristics concerning a plurality of color imaging systems and spectral characteristics concerning a plurality of illumination lights in accordance with this choice. Therefore, since the color imaging system or the illumination light can be selected, applicability as the system can be improved, thereby enabling utilization for various purposes.

Further, the inverse matrix of the system matrix based on the dedicated base vector of the subject as the identification target and the spectral characteristic of the imaging system is calculated, the coefficient concerning the dedicated base vector of the subject as the identification target is selected from this inverse matrix, and the weighting factor concerning the dedicated base vector of the subject as the identification target is calculated based on the selected coefficient and the image signal. Therefore, since the weighting factor concerning the dedicated base vector, i.e., the identification target is calculated by the signal processing based on the known spectral characteristic of the subject as the identification target and the spectral characteristic of the imaging system, an error due to the signal processing hardly occurs, and reliable identification can be carried out. Further, since the system matrix is configured to include the dedicated base vectors of the non-identification-target subjects, the signal processing using the dedicated base vectors of the non-identification-target subjects can be applied to a region where the subject as the identification target is not present, i.e., a region where a subject which is not the identification target is present as required, thereby improving a freedom degree in the subsequent processing of calculating an output signal.

Further, since the output signal is obtained by normalizing the weighting factor concerning the dedicated base vector based on the known spectral characteristic of the subject as the identification target, the highly accurate output signal can be obtained in regard to presence of the identification target. Furthermore, since the output signal is obtained by the normalization processing alone, an increase in speed of the processing and a reduction in cost can be achieved.

It is to be noted that the example of processing a video image has been described, but a still image can be acquired in accordance with an operation of a non-illustrated shutter button of the external interface unit 119 and the same processing can be of course applied to the acquired still image.

[Modification 1]

It is to be noted that such dedicated base vectors as shown in FIG. 4 are used as the base vectors in the first embodiment, the present invention does not have to be restricted to such a configuration.

For example, as shown in FIG. 7, it is possible to adopt a configuration using a dedicated base vector (O1($\lambda$) based on known spectral characteristic of a subject as an identification target and general-purpose base vectors (O2($\lambda$), O3($\lambda$)) used for estimation of spectral characteristics of arbitrary subjects. In the drawing, the dedicated base vector is indicated by a heavy line and the general-purpose base vectors are indicated by thin lines. This FIG. 7 shows an example of using higher-order base vectors having high contribution ratios which are selected by principal component analysis of spectral reflectance characteristics of, e.g., color samples of Munsell color system and stored in the base vector ROM 114 as the general-purpose vectors (O2($\lambda$), O3($\lambda$)). On the other hand, as described in the first embodiment, as the dedicated base vector (O1($\lambda$)), a subject as an identification target, e.g., oxyhemoglobin voluminously contained a vessel region that is important in a diagnosis using an endoscope is selected from a plurality of dedicated base vectors stored in the base vector ROM 114 based on a setting configured through the external interface unit 119. The general-purpose base vectors (O2($\lambda$), O3($\lambda$)) can be used for the subsequent processing of calculating an output signal since the signal processing using the base vectors can be applied to a region where the subject as the identification target is not present, i.e., a region where a subject which is riot the identification target is present as required.

FIG. 8 is a view showing three types of base vectors when deoxyhemoglobin is used as the dedicated base vector (O1($\lambda$)). It is to be noted that the dedicated base vector is indicated by a heavy line and each general-purpose base vector is indicated by a thin line.

All dedicated base vectors based on known spectral characteristics of subjects do not have be used as base vectors, and the same effects as those of the first embodiment can be obtained even if at least the dedicated base vector of the subject as the identification target is used and the general-purpose base vectors are used for estimation of spectral characteristics of arbitrary subjects.

Further, signal processing using the general-purpose base vectors can be applied to a region other than the identification target, whereby a freedom degree in the subsequent processing of calculating an output signal can be improved.

Furthermore, an inverse matrix of a system matrix based on the general-purpose base vectors, the dedicated base vector, and a spectral characteristic of the imaging system is calculated, a coefficient concerning the dedicated base vector is selected from this inverse matrix, and a weighting factor concerning the dedicated base vector is calculated based on the selected coefficient and an image signal. Therefore, since the weighting factor concerning the dedicated base vector, i.e., the identification target is calculated by the signal processing based on the known spectral characteristic of the subject as the identification target and the spectral characteristic of the imaging system, an error due to the signal processing hardly occurs, and reliable identification can be carried out. Moreover, since the configuration where the system matrix includes the general-purpose base vectors is adopted, the signal processing using the general-purpose base vectors can be applied to a region where the subject as the identification target is not present as required, i.e., a region where a subject other than the identification target is present, thereby improving a freedom degree in the subsequent processing of calculating an output signal.

[Modification 2]

Additionally, although the single CCD having the Bayer type primary color filter 120 including the three color filters 121R, 121G, and 121B of R, G, and B arranged on a front surface thereof is assumed as the imaging system in the first embodiment, the present invention is not restricted to such as configuration. For example, the present invention can be also applied to a single CCD having a primary color filter including four color filters or a color-difference line sequential type complementary filter arranged on a front surface thereof, two CCDs, or three CCDs.

As shown in FIG. 9, a primary color filter 122 including four color filters has a configuration where a basic unit is 2×2 pixels, and four color filters 121R, 121Gr, 121Gb, and 121B of R, Gr, Gb, and B are arranged in the basic unit in association with each pixel.

Furthermore, as shown in FIG. 10, a color-difference sequential type complementary filter 123 has 2×2 pixels as a basic unit, and a cyan (Cy) color filter 121Cy, a magenta (Mg) color filter 121 Mg, a yellow (ye) color filter 121Ye, and a green (G) color filter 121G are arranged in the basic unit in association with each pixel. However, positions of the Mg color filter 121Mg and the G color filter 121G are reversed in accordance with each line. Spectral sensitivity characteristics $(SCy(\lambda), SMg(\lambda), SYe(\lambda), SG(\lambda))$ of a color imaging system in an example where this color-difference sequential type complementary filter 123 is used is as shown in FIG. 11, for example.

A configuration using a single image acquisition element having the Bayer type primary color filter 120 or the color-difference line sequential type complementary filter 123 arranged on a front surface thereof has high affinity with respect to a conventional imaging system, and it can be applied to many imaging systems.

Furthermore, it is also possible to adopt a configuration where a plurality of characteristics are recorded in the system spectral characteristic ROM 115 as spectral characteristics concerning the color imaging systems and spectral characteristics concerning illumination light used at the time of image acquisition of subjects and characteristics used for actual image acquisition are selected.

In case of the four-color filters 122 and 123 shown in FIG. 9 and FIG. 10, a total number of the dedicated base vectors and the general purpose-base vectors is 4. In case of the four-color filter, each of the system matrix M represented in expression (1) and the inverse matrix $M^{-1}$ of the system matrix M represented in expression (2) has a 4×4 size. Moreover, a right-hand side of expression (3) also has a conformation having a fourth term added thereto.

Each of FIG. 12 and FIG. 13 shows an example of dedicated base vectors and general-purpose base vectors which are four in total.

FIG. 12 includes one dedicated base vector $(O1(\lambda))$ and three general-purpose base vectors $(O2(\lambda), O3(\lambda), O4(\lambda))$. In the drawing, the dedicated base vector is indicated by a heavy line, and the general-purpose base vectors are indicated by thin lines. The general-purpose base vectors are stored in the base vector ROM 114 by principal component analysis of spectral reflectance characteristics of, e.g., color samples of Munsell color system and selecting three higher-order base vectors having high contribution ratios The dedicated base vector corresponds to the oxyhemoglobin shown in FIG. 4.

On the other hand, FIG. 13 includes two dedicated base vectors $(O1(\lambda), O2(\lambda)$ and two general-purpose vectors $(O3(\lambda), O4(\lambda))$. In the drawing, the dedicated base vectors are indicated by heavy lines, and the general-purpose base vectors are indicated by thin lines. The two dedicated base vectors correspond to the oxyhemoglobin and the deoxyhemoglobin shown in FIG. 4.

It is to be noted that all dedicated base vectors based on known spectral characteristics of subjects can be used as the base vectors as described above. Moreover, this configuration can be of course applied to both a video image and a still image.

[Modification 3]

Additionally, the first embodiment has the configuration where the changeover unit 113 selects and outputs one of an ordinary frame signal transferred from the signal processing unit 111 and a frame signal concerning presence of an identification target transferred from the normalization unit 116 as an output of an image signal. However, the present invention does not have to be restricted to such a configuration For example, as shown in FIG. 11, the normalization unit 116 may be omitted from the configuration depicted in FIG. 1, and the changeover unit 113 may be substituted by an emphasis unit 124. A basic configuration is equivalent to that in FIG. 1, and like reference names and like reference numerals denote like configurations. Different points alone will be described hereinafter.

A signal processing unit 111 and a calculation unit 112 are connected to the emphasis system 124. The emphasis unit 124 is connected to an output unit 117. A control unit 118 is bi-directionally connected with the emphasis unit 124. To the emphasis unit 124 are transferred an ordinary frame signal from the signal processing unit 111 and a weighting factor concerning a dedicated base vector based on a known spectral characteristic of a subject as an identification target from the calculation unit 112.

In such a configuration, the emphasis unit 124 executes emphasis processing with respect to the frame signal transferred from the signal processing unit 111 based on the weighting factor transferred from the calculation unit 112 under control of the control unit 118. As the emphasis processing, known edge emphasis processing or chrome emphasis processing is assumed, and it is carried out in such a mariner that an emphasis amount thereof is proportionate to the weighting factor. The frame signal subjected to the emphasis processing is transferred to the output unit 117. In this manner, the emphasis unit 124 and the output unit 117 function as an output signal calculation unit that calculates an output signal as an identification result of a subject as an identification target based on the weighting factor concerning the dedicated base vector, for example.

As described above, when the emphasis processing is executed from the weighting factor concerning the dedicated base vector based on spectral characteristic of the subject as the identification target, a region where the subject as the identification target, e.g., oxyhemoglobin is present alone is emphasized, thereby improving recognition ability. Furthermore, in regard to a region where the subject as the identification target is not present, i.e., a region where a subject other than the identification target is present, since an image signal subjected to ordinary processing is output, overall image signals can be readily recognized, thus improving operability for a user.

It is to be noted that general-purpose base vectors used for estimation of spectral characteristics of arbitrary subjects may be utilized as long as at least the dedicated base vector of the subject as the identification target is used as described above. Moreover, a total number of the base vectors is not restricted to 3 as described in Modification 2, and it may coincide with a number of types of filters that pass image signal from the color imaging system therethrough. Additionally, this configuration can be of course applied to both a video image and a still image.

[Modification 4]

Further, as shown in FIG. 15, in the configuration depicted in FIG. 1, the changeover unit 113 may be substituted by a combination unit 125. A basic configuration is equivalent to FIG. 1, and like names and like reference numerals denote like structures. Different points alone will be described hereinafter.

A signal processing unit 111 and a normalization unit 116 are connected to the combination unit 125. The combination unit 125 is connected to an output unit 117. A control unit 118 is bi-directionally connected with the combination unit 125. To the combination unit 125 are transferred an ordinary frame signal that is transferred from the signal processing unit 111 and a frame signal concerning presence of an identification target from the normalization unit 116.

In such a configuration, the combination unit 125 combines the frame signal concerning presence of the identification target transferred from the normalization unit 116 to the frame signal transferred from the signal processing unit 111 under control of the control unit 118. As the combination processing, processing such as known superimposition can be assumed. The combined frame signal is transferred to the output unit 117. In this manner, the normalization unit 116, the combination unit 125, and the output unit 117 function as an output signal calculation unit that calculates an output signal as an identification result of a subject as the identification target based on a weighting factor concerning a dedicated base vector.

As described above, when the weighting factor concerning the dedicated base vector based on a known spectral characteristic of the subject as the identification target is normalized to obtain an image signal concerning the identification target, an accurate output signal can be obtained in regard to a region where the subject as the identification target is present. Furthermore, since the obtained image signal concerning the identification target is combined with an image signal subjected to ordinary processing, the image signal subjected to ordinary processing is likewise output in regard to a region where the subject as the identification target is not present, i.e., a region where a subject other than the identification target is present, and overall image signals can be easily recognized, thereby improving operability for a user.

Moreover, the combination unit 125 may execute combination processing such as known picture-in-picture for displaying a window in a part of a screen to show a frame signal from the signal processing unit 111 or a frame signal from the normalization unit 116 as a child screen. In this case, it is preferable to enable selecting a parent screen and a child screen based on an instruction supplied via an external interface unit 119.

It is to be noted that, in this modification, dedicated base vectors may be entirely used, or at least a dedicated base vector of the subject as an identification target may be used and general-purpose base vectors may be used for other subjects. Moreover, a total number of base vectors is not restricted to 3 as described above. Additionally, this configuration can be of course applied to both a video image and a still image.

[Modification 5]

Figure 16:
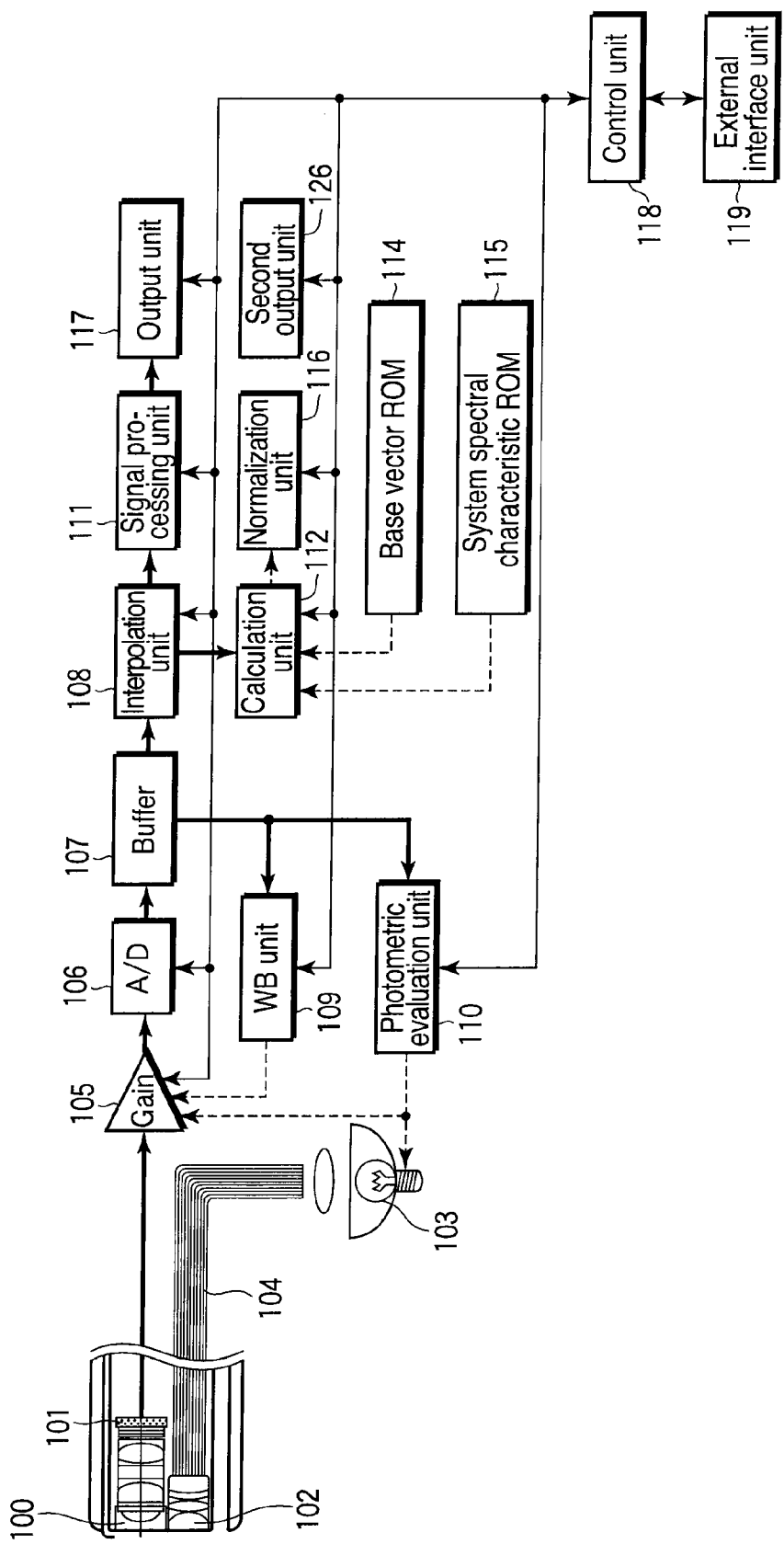
FIG. 16 is a view showing a configuration of an endoscope to which a signal processing system according to Modification 5 of the first embodiment is applied.

Further, as shown in FIG. 16, the changeover unit 113 may be omitted from the configuration shown in FIG. 1, and a second output unit 126 different from the output unit 117 may be added. A basic configuration is equivalent to FIG. 1, and like names and like reference numerals denote like structures. Different points alone will now be described hereinafter.

A signal processing unit 111 is connected to the output unit 117. A normalization unit 116 is connected to the second output unit 126. A control unit 118 is hi-directionally connected with the second output unit 126. The signal processing unit 111 transfers an ordinary frame signal to the cutout unit 117 under control of the control unit 118. In the output unit 117, the ordinary frame signal is displayed. The normalization unit 116 transfers a frame signal concerning presence of an identification target to the second output unit 126 under control of the control unit 118. In the second output unit 126, the frame signal concerning presence of the identification target is displayed. In this manner, the normalization unit 116, the output unit 117, and the second output unit 126 function as an output signal calculation unit that calculates an output signal as an identification result of a subject as the identification target based on a weighting factor concerning a dedicated base vector.

As described above, when an image signal concerning the identification target is obtained by normalizing the weighting factor concerning the dedicated base vector based on a known spectral characteristic of the subject as the identification target, an accurate output signal can be obtained in regard to presence of the identification target. Furthermore, since each image signal subjected to ordinary processing is also independently output, overall image signals can be easily recognized, thus improving operability for a user.

It is to be noted that dedicated base vectors may be entirely used, or at least a dedicated base vector of the subject as the identification target may be used and general-purpose base vectors may be used for other subjects. Moreover, a total number of the base vectors is not restricted to 3 as described above. Additionally, this configuration can be of course applied to both a video image and a still image.

[Modification 6]

Further, in the first embodiment, the signal processing system is integrated with the image acquisition unit formed of the imaging lens system 100, the CCD 101, the illumination lens system 102, the illumination light source 103, the optical fiber 104, the amplification unit 105, the analog-to-digital converter 106, the WB unit 109, and the photometric evaluation unit 110. However, the present invention does not have to be restricted to such a configuration.

For example, associated information concerning an image acquisition condition such as a subject as an identification target, a color imaging system, or illumination light can be recorded in a header portion of an image signal acquired by a different image acquisition unit in an unprocessed Raw data format, and this signal can be stored in a recording medium such as a hard disk or a memory card, and it can be read out to be processed. Alternatively, such image signal transmitted wirelessly or through a cable network can be received and processed.

Figure 17:
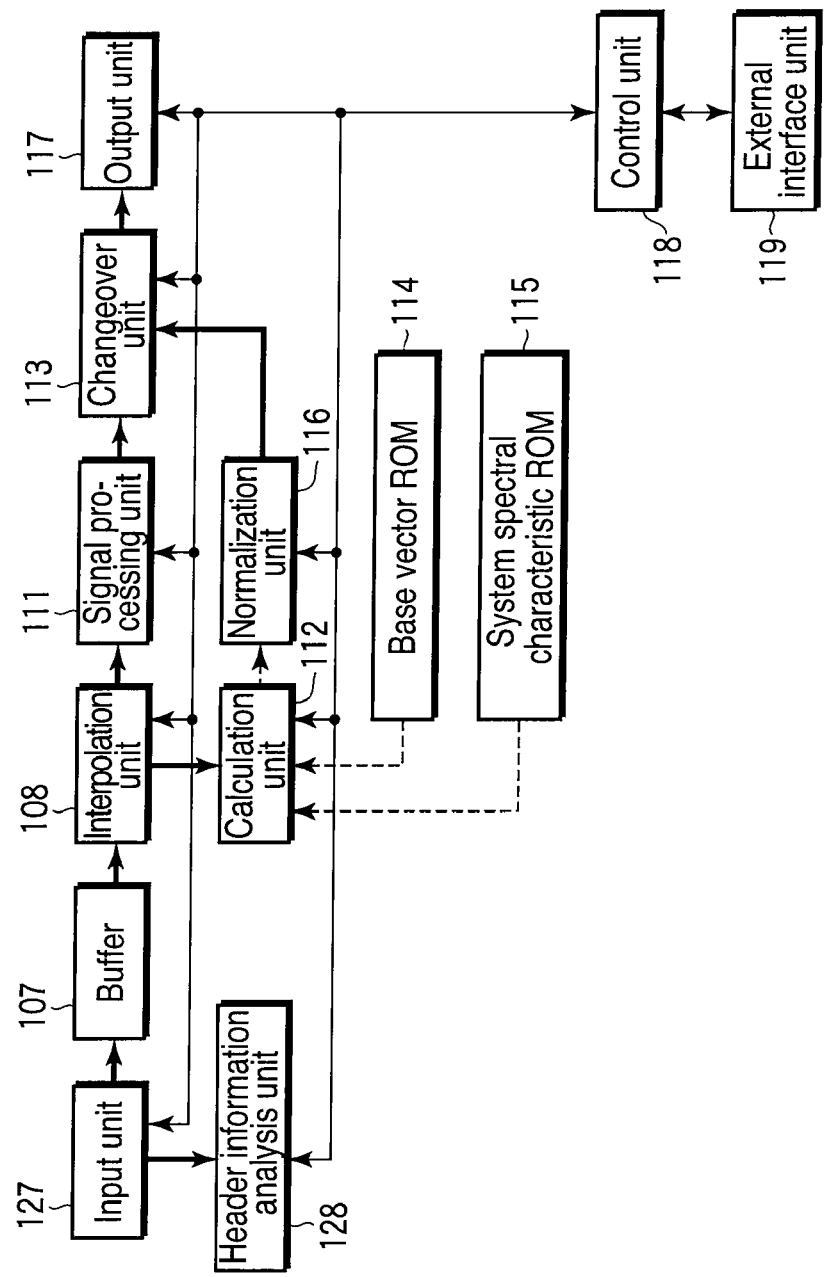
FIG. 17 is a view showing a configuration of an endoscope to which a signal processing system according to Modification 6 of the first embodiment is applied.

In this case, as shown in FIG. 17, the imaging lens system 100, the CCD 101, the illumination lens system 102, the illumination light source 103, the optical fiber 104, the amplification unit 105, the analog-to-digital converter 106, the WE unit 109, and the photometric evaluation unit 110 are omitted from the configuration shown in FIG. 1, and an input unit 127 and a header information analysis unit 128 are added. A basic configuration is equivalent to FIG. 1, and like names and like reference numerals denote like structures. Different points alone will now be described hereinafter.

The input unit 127 is connected to a buffer 107 and the header information analysis unit 128. A control unit 118 is bi-directionally connected with the input unit 127 and the header information analysis unit 128. When a reproducing operation is started through an external interface unit 119 such as a mouse or a keyboard, signals and header information stored in a recording medium such as a hard disk or a memory card or signals and header information received through a network are read from the input unit 127. It is to be noted that image signals are sequentially read one by one at predetermined time intervals, i.e., one-frame time intervals in this modification. Each signal from the input unit 127 is transferred to the buffer 107, and the header information is transferred to the header information analysis unit 128. The header information analysis unit 128 extracts information at the time of image acquisition from the header information and transfers the extracted information to a control unit 118. Subsequent processing is equivalent to that shown in FIG. 1.

It is to be noted that dedicated base vectors may be entirely used, or at least a dedicated base vector of a subject as an identification target may be used whilst, general-purpose base vectors may be used for other subjects. Moreover, a total number of base vectors is not restricted to 3, and it may coincide with the number of types of filters that pass acquired image signals therethrough. Additionally, this configuration can be of course applied to both a video image and a still image.

[Modification 7]

Further, the processing using the hardware is premised in the first embodiment, but the present invention does not have to be restricted to such a configuration. For example, it is possible to adopt a configuration that an image signal from the CCD 101 takes a Raw data format without being subjected to processing, an image acquisition condition such as a subject as an identification target, the color imaging system, illumination light, and others is output as header information from the control unit 118, and the image signal and the header information are input to a non-illustrated computer to be processed by software.

Software processing as the signal processing using the non-illustrated computer will now be described hereinafter with reference to FIG. 18.

That is, the computer first receives an image signal and header information concerning an image acquisition condition such as a subject which is an identification target, the color imaging system, illumination light, and others (step S101). It is to be noted that processing an image signal from a Bayer type single CCD including three color filters 121R, 121G, and 121B is assumed in this modification. Furthermore, here, an example using a dedicated base vector (O1($\lambda$)) and general-purpose base vectors (O2($\lambda$), O3($\lambda$) like Modification 1 will be explained.

After the step S101, a plurality of dedicated base vectors and a plurality of general-purpose base vectors are input (step S102), and a plurality of light source spectral luminance characteristics and a plurality of color imaging system spectral sensitivity characteristics are input (step S103). Here, the plurality of base vectors and the plurality of spectral characteristics are input by being read out from a recording medium provided in the computer or a detachable recording medium or being read out through a network.

Furthermore, based on calculation processing which will be described later in detail, predetermined coefficients of an inverse matrix $M^{-1}$ of a system matrix M used for calculating a weighting factor concerning the dedicated base vector (O1 ($\lambda$)), i.e., elements $m_{11}$, $m_{12}$, and $m_{13}$ are calculated (step S104). Thereafter, frame signals are sequentially extracted from the input an image signal (step S105), and three color frame signals are generated by known interpolation processing (step S106). Moreover, signal processing such as known gradation processing or emphasis processing is carried out with respect to these frame signals (step S107).

Additionally, a weighting factor ($w1_{ij}$) concerning the dedicated base vector (O1($\lambda$)) is calculated as represented by expression (3) simultaneously with the signal processing at the step S107 (step S108), and a frame signal concerning presence of an identification target is generated by normalizing the calculated weighting factor ($w1_{ij}$) (step S109).

Further, one of the ordinary frame signal obtained at the step S107 and the frame signal concerning presence of a subject as the identification target obtained at the step S109 is changed over (step S110), and the frame signal is output to a non-illustrated display monitor or the like connected to the computer (step S111). Then, whether all frame signals are completed is judged (step S112), and the processing returns to the step S105 when they are not completed, or the processing is terminated when they are completed.

The calculation processing at the step S104 is carried out as shown in FIG. 19.

First, data to be used is selected from the plurality of dedicated base vectors and the plurality of general-purpose base vectors input at the step S102 and the plurality of light source spectral luminance characteristics and the plurality of color imaging system spectral sensitivity characteristics input at the step S103 (step S201). This operation selects a dedicated base vector, general-purpose base vectors, a light source spectral luminance characteristic, and color imaging system spectral sensitivity characteristics based on an image acquisition condition such as a subject which is an identification target, the color imaging system, illumination light, and others in the header information input at the step S101. For example, the operation selects such a dedicated base vector (O1($\lambda$)) and general-purpose base vectors (O2($\lambda$), O3($\lambda$)) as shown in FIG. 7, such spectral luminance characteristic of the light source as shown in FIG. 5, and such spectral sensitivity characteristics of the color imaging system as shown in FIG. 6.

Thereafter, the system matrix M represented by expression (1) is calculated (step 1202), and the inverse matrix $M^{-1}$ of the system matrix M is further calculated (step S203). Furthermore, the elements $m_{11}$, $m_{12}$, and $m_{13}$ of the inverse matrix $M^{-1}$ required for calculating the weighting factor ($w1_{ij}$) of the dedicated base vector (O1($\lambda$) are selected as the predetermined coefficients (step S204), and the selected elements $m_{11}$, $m_{12}$, and $m_{13}$ of the inverse matrix $M^{-1}$ are output (step S205).

It is to be noted that the example where the processing associated with Modification 1 is carried out by software has been described here, and it is needless to say that processing like the first embodiment and Modifications 2 to 6 can be likewise carried out by software.

Moreover, this configuration can be of course applied to both a video image and a still image. In case of a still image, the judgment at the step S112 is omitted to terminate the processing.

Second Embodiment

A second embodiment according to the present invention will now be described.

(Configuration)

As shown in FIG. 20, an endoscope to which a signal processing system according to a second embodiment of the present invention is applied has a configuration that an imaging system ROM 129, an illumination system ROM 130, a second calculation unit 131, a second normalization unit 132, a falsely-colored processing unit 133 are added to the configuration of the first embodiment depicted in FIG. 1. A basic configuration is equivalent to that of the first embodiment, and like names and like reference numerals denote like structures. Different points alone will be described hereinafter.

In this embodiment, the imaging system ROM 129 included in an endoscope main body and the illumination system ROM 130 included in an illumination main body are connected to a control unit 118. An interpolation unit 108 is connected to a signal processing unit 111, a calculation unit 112, and a second calculation unit 131. A base vector ROM 114 and a system spectral characteristic ROM 115 are connected to a calculation unit 112 and the second calculation unit 131. The second calculation unit 131 is connected to the second normalization unit 132. A normalization unit 116 and the second normalization unit 132 are connected to the falsely-colored processing unit 133. The falsely-colored processing unit 133 is connected to a changeover unit 113. The control unit 118 is bi-directionally connected to the second calculation unit 131, the second normalization unit 132, and the falsely-colored processing unit 133.

(Function)

A function of the signal processing system according to this embodiment is basically equivalent to that of the first embodiment, and different points alone will be described.

In FIG. 20, a flow of signals will be explained. The control unit 118 sets an image acquisition condition such as a subject which is an identification target through an external interface unit 119, a color imaging system based on information from the imaging system ROM 129, and illumination light based on information from the illumination system ROM 130, respectively. Here, when selecting one color imaging system and one illumination system from a plurality of color imaging systems and a plurality of illumination lights, previously storing information required to specify each imaging system and each illumination system in the imaging system and the illumination system as ROMs enables eliminating the need for a selecting operation performed by a user via the external interface unit 119. Further, when spectral characteristic concerning a color imaging system used for image acquisition of subjects including the subject as the identification target is stored in the imaging system ROM 129 and spectral characteristic concerning illumination light used for image acquisition of each subject by the color imaging system is stored in the illumination system ROM 130, respectively, the system spectral characteristic ROM 115 can be omitted, or the processing can cope with a novel imaging system or illumination system that is not stored in the system spectral characteristic ROM 115.

Like the first embodiment, the interpolation unit 108 reads single three-color frame signal from a buffer 107 under control of the control unit 118 and executes known interpolation processing to generate three color frame signals. The generated three color frame signals are sequentially transferred to the signal processing unit 111, the calculation unit 112, and the second calculation unit 131 in units of frame signal. The signal processing unit 111, the calculation unit 112, the normalization unit 116, the second calculation unit 131, the second normalization unit 132, and the falsely-colored processing unit 133 on subsequent stages are synchronized in units of each frame signal to execute processing under control of the control unit 118.

The signal processing unit 111 executes known gradation processing and emphasis processing with respect to each frame signal transferred from the interpolation unit 108 and transfers the processed frame signal to the changeover unit 113 under control of the control unit 118.

Moreover, like the first embodiment, the calculation unit 112 calculates a weighting factor concerning a dedicated vector based on the subject as the identification target, e.g., oxyhemoglobin shown in FIG. 7 and transfers the calculated weighting factor to the normalization unit 116. The normalization unit 116 normalizes the weighting factor transferred from the calculation unit 112 so that this factor can coincide with a signal level of an image signal and transfers the processed weighting factor to the falsely-colored processing unit 133 as a frame signal concerning presence of the identification target under control of the control unit 118.

Likewise, the second calculation unit 131 reads a dedicated base vector based on known spectral characteristic of the subject as the identification target and general-purpose base vectors used for estimating spectral characteristics of arbitrary subjects shown in FIG. 7 from the base vector ROM 114 under control of the control unit 118. Additionally, this unit also reads a spectral characteristic of the imaging system including a spectral characteristic concerning the illumination light used for image acquisition of subjects by the color imaging system shown in FIG. 5 and spectral characteristic concerning the color imaging system shown in FIG. 6 from the system spectral characteristic ROM 115 under control of the control unit 118. Then, in regard to each frame signal transferred from the interpolation unit 108, weighting factors concerning the general-purpose base vectors are calculated by using the dedicated base vector, the general-purpose base vectors, the spectral characteristic concerning the color imaging system, and the spectral characteristic concerning the illumination light. The calculated weighting factors of the general-purpose base vectors are transferred to the second normalization unit 132. The second normalization unit 132 normalizes the weighting factors transferred from the second calculation unit 131 so that these factors can coincide with a signal level of the image signal under control of the control unit 118. Additionally, this unit transfers the processing weighting factors to the falsely-colored processing unit 133 as frame signals concerning a region where the identification target is not present, i.e., a region where subjects other than the identification target are present.

The falsely-colored processing unit 133 executes falsely-colored processing from the frame signal transferred from the normalization unit 116 and the frame signals transferred from the second normalization unit 132 under control of the control unit 118. The falsely-colored processing is carried out by assigning the frame signal that is transferred from the normalization unit 116 and concerns presence of the identification target to an R signal and assigning the frame signals that are transferred from the second normalization unit 132 and concern the region where the subject as the identification target is not present, i.e., the region where the subjects other than the identification target are present to a G or B signal. The frame signal subjected to the falsely-colored processing is transferred to the changeover unit 113.

The changeover unit 113 selects one of the ordinary frame signal transferred from the signal processing unit 111 and the frame signal transferred from the falsely-colored processing unit 133 and subjected to the falsely-colored processing and transfers the selected signal to an output unit 117 which is, e.g., a display monitor to be displayed under control of the control unit 118. It is to be noted that the output unit 117 is not restricted to the display monitor, and it can take a conformation of sequentially recording and storing each frame signal in a recording medium such as a hard disk or a memory card. In this manner, the normalization unit 116, the second normalization unit 132, the falsely-colored processing unit 133, the changeover unit 113, and the output unit 117 function as an output signal calculation unit that calculates an output signal as an identification result of the subject which is the identification target based on the weighting factor concerning the dedicated base vector, for example.

Figure 21:
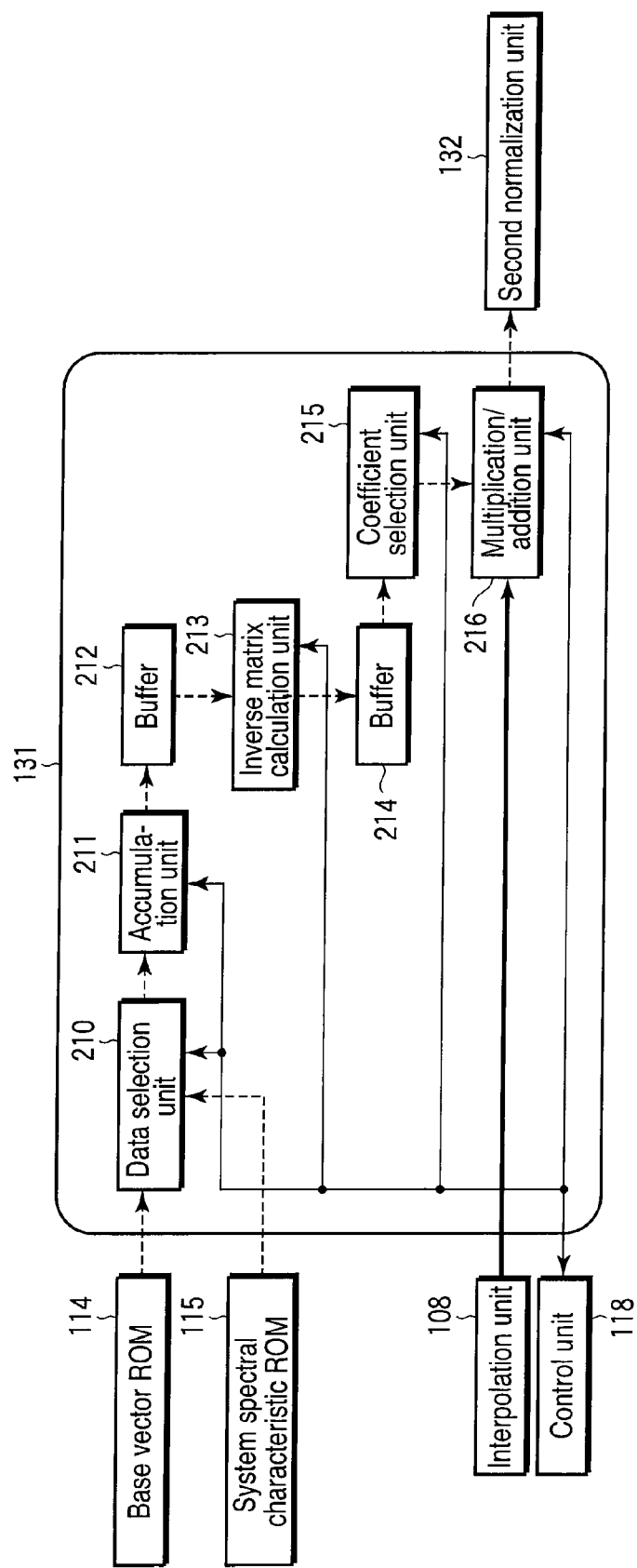
FIG. 21 is a view showing an example of a configuration of a second calculation unit in FIG. 20.

As shown in FIG. 21, the second calculation unit 131 is constituted of a data selection unit 210, an accumulation unit 211, a buffer 212, an inverse matrix calculation unit 213, a buffer 214, a coefficient selection unit 215, and a multiplication/addition unit 216. The base vector ROM 114 and the system spectral characteristic ROM 115 are connected to the data selection unit 210. The data selection unit 210 is connected to the coefficient selection unit 215 through the accumulation unit 211, the buffer 212, the inverse matrix calculation unit 213, and the buffer 214. The coefficient selection unit 215 and the interpolation unit 108 are connected to the multiplication/addition unit 216. The multiplication/addition unit 216 is connected to the second normalization unit 132. The control unit 118 is bi-directionally connected to the data selection unit 210, the accumulation unit 211, the inverse matrix calculation unit 213, the coefficient selection unit 215, and the multiplication/addition unit 216.

The data selection unit 210 receives from the control unit 118 information of a subject as an identification target set through the external interface unit 119. Further, based on this information, the data selection unit 210 reads a dedicated base vector (O1($\lambda$)) based on a spectral characteristic of the subject as the identification target shown in FIG. 7 and general-purpose base vectors (O2($\lambda$), O3($\lambda$)) used for estimating spectral characteristics of arbitrary subjects from the base vector ROM 114. In this manner, the base vector ROM 114 and the data selection unit 210 function as a base vector acquisition unit that acquires a dedicated base vector based on known spectral characteristic of the subject as the identification target, for example. Furthermore, the data selection unit 210 receives from the control unit 118 information of a color imaging system set based on information from the imaging system ROM 129 and information of illumination light set based on information from the illumination system ROM 130. Moreover, based on the information, the data selection unit 210 reads a spectral luminance characteristic (I($\lambda$)) of the light source shown in FIG. 5 and spectral characteristics (SR($\lambda$), SC($\lambda$), SB($\lambda$)) concerning the color imaging system shown in FIG. 6 from the system spectral characteristic ROM 115. In this manner, the imaging system ROM 129, the illumination system ROM 130, and the data selection unit 210 function as a system spectral characteristic acquisition unit that acquires spectral characteristic of the imaging for example. The dedicated base vector (O1($\lambda$), the general-purpose base vectors (O2($\lambda$), O3($\lambda$), the spectral luminance characteristic (I($\lambda$)) of the light source, and the spectral sensitivity characteristics (SR($\lambda$) SG($\lambda$), SB($\lambda$) of the color imaging system are transferred to the accumulation unit 211.

The accumulation unit 211 calculates a system matrix M concerning the imaging system having the 3×3 size represented by expression (1) under control of the control unit 118. In this manner, the data selection unit 210 and the accumulation unit 211 function as a matrix calculation unit that calculates the system matrix concerning the imaging system, for example. The calculated system matrix M is transferred to and stored in the buffer 212. The inverse matrix calculation unit 213 reads the system matrix M from the buffer 212 and calculates an inverse matrix $M^{-1}$ thereof under control of the control unit 118. The calculated inverse matrix $M^{-1}$ is transferred to and stored in the buffer 214.

Using the inverse matrix $M^{-1}$ of the system matrix M and frame signals consisting of R, G, and B enables obtaining weighting factors (w1, w2, w3) concerning the dedicated base vector (O1($\lambda$)) and the general-purpose base vectors (O2($\lambda$), O3($\lambda$)) in units of each pixel as represented by expression (2). In this second calculation unit 131, obtaining the weighting factors (w2, w3) concerning the general-purpose base vectors (O2($\lambda$), O3($\lambda$)) is assumed. Therefore, coefficients required for the inverse matrix $M^{-1}$ of the system matrix represented by expression (2) are six elements $m_{21}$, $m_{22}$, $m_{23}$, $m_{31}$, $m_{32}$, and $m_{33}$.

Thus, the coefficient selection unit 215 selects the elements $m_{21}$, $m_{22}$, $m_{23}$, $m_{31}$, $m_{32}$, and $m_{33}$ of the inverse matrix $M^{-1}$ of the system matrix M from the buffer 214 and transfers them to the multiplication/addition unit 216 under control of the control unit 118. After the elements $m_{21}$, $m_{22}$, $m_{23}$, $m_{31}$, $m_{32}$, and $m_{33}$ of the inverse matrix $M^{-1}$ of the system matrix M are transferred from the coefficient selection unit 205, the multiplication/addition unit 216 reads each frame signal from the interpolation unit 108 in units of pixel consisting of R, G, and B under control of the control unit 118. Further, the multiplication/addition unit 216 obtains weighting factors ($w2_{ij}$, $w3_{ij}$) concerning the general-purpose base vectors (O2($\lambda$), O3($\lambda$)) based on the following expression (4) and the above expression (5).

$$w2_{ij}=m_{21}\cdot R_{ij}+m_{22}\cdot G_{ij}+m_{23}\cdot B_{ij} \quad (4)$$

$$w3_{ij}=m_{31}\cdot R_{ij}+m_{32}\cdot G_{ij}+m_{33}\cdot B_{ij} \quad (5)$$

The weighting factors ($w2_{ij}$, $w3_{ij}$) are transferred to the second normalization unit 132.

It is to be noted that a configuration of the second calculation unit 131 is basically equivalent to that of the calculation unit 112 described in the first embodiment. Therefore, both the calculation units can be integrated so that one calculation unit can calculate all weighting factors concerning the dedicated base vector and the general-purpose vectors.

Further, in the second calculation unit 131, like the calculation unit 112, a dedicated base vector of a subject having a known spectral characteristic rather than a general-purpose normalization vector may be used together with the dedicated base vector of the subject as the identification target.

As described above, according to this second embodiment, on the basis of the dedicated base vector based on a known spectral characteristic of the subject as the identification target, the dedicated base vector based on a know spectral characteristic of a non-identification-target subject which is not the identification target or the general-purpose base vector used for estimating a spectral characteristic of an arbitrary subject, the spectral characteristic concerning the color imaging system used for image acquisition of subjects including the subject as the identification target, and the spectral characteristic concerning the illumination light used at the time of image acquisition of subjects by the color imaging system, the weighting factor concerning the dedicated base vector of the subject as the identification target that takes a value proportionate to presence of the subject identification target and the weighting factor concerning the dedicated base vector of the non-identification-target subject or the general-purpose base vector are calculated, and an output signal is calculated based on both the weighting factors.

Therefore, like the first embodiment, since using the dedicated base vector based on the known spectral characteristic of the subject as the identification target enables calculating the weighting factor that takes a value which is proportionate to presence of the subject as the identification target, signal processing including an error like approximation based on the conventional least-square method does not have to be executed. Accordingly, an error due to the signal processing hardly occurs, and the subject as the identification target can be reliably identified. Further, since the ordinary broadband illumination light is used, an influence of noise can be suppressed, thereby enabling stable identification. Furthermore, since the output signal is directly calculated from the weighting factor concerning the dedicated base vector, an increase in speed of the processing and a reduction in cost can be achieved.

Furthermore, since the image signal concerning the identification target is obtained by normalizing the weighting factor concerning the dedicated base vector based on the known spectral characteristics of the subject as the identification target, the accurate output signal can be obtained in regard to presence of the identification target.

It is to be noted that, like the first embodiment, this configuration can be applied to the imaging system constituted of the four primary color filters 122 or the color-difference line sequential type complementary filter 123 or to two CCDs or three CCDs. In this case, it is possible to use the dedicated base vectors and the general-purpose base vectors shown in FIG. 8, FIG. 12, and FIG. 13 or use the dedicated base vectors alone. When the dedicated base vectors alone are used, the falsely-colored processing unit 133, the changeover unit 113, and the output unit 117 function as a falsely-colored processing signal calculation unit that calculates a false color signal as an output signal from a weighting factor concerning a dedicated base vector of a subject as an identification target and a weighting factor concerning a dedicated base vector of each subject which is not the identification target, both the vectors being normalized by the normalization unit 116. Further, this configuration can be of course applied to both a video image and a still image.

As described above, a region other than an identification target is subjected to falsely-colored display together with a signal obtained by normalizing a weighting factor concerning a dedicated base vector based on a known spectral characteristic of a non-identification-target subject or a weighting factor concerning a general-purpose base vector, thereby facilitating recognition of entire image signals and improving operability with respect to a user.

Furthermore, since the weighting factor concerning the dedicated base vector of the non-identification-target subject or the weighting factor concerning the general-purpose base vector is calculated in regard to a region where the subject as the identification target is not present, i.e., a region where the non-identification-target subject is present, signal processing is executed with respect to the entire screen, thus easily securing uniformity and continuity with respect to the identification target.

Moreover, the weighting factor concerning the dedicated base vector of the subject as the identification target and the weighting factor concerning the dedicated base vector of the non-identification-target subject are calculated from the dedicated base vector based on the known spectral characteristic of the subject as the identification target, the dedicated base vector based on the known spectral characteristic of the subject which is not the identification target, the spectral characteristic concerning the color imaging system used for image acquisition of subjects, and a spectral characteristic concerning the illumination light used for image acquisition of the subjects, and an output signal is calculated based on both the weighting factors. Therefore, since the dedicated base vector based on the known spectral characteristic of the subject as the identification target is used, an error due to the signal processing rarely occurs, and reliable identification can be carried out. Additionally, the signal processing using the dedicated base vector of the non-identification-target subject can be applied to a region other than the identification target, thereby improving a freedom degree in the processing of calculating an output signal.

[Modification 1]

Further, the second embodiment is configured to select and output one of an ordinary frame signal transferred from the signal processing unit 111 and a frame signal that is subjected to falsely-colored processing and transferred from the falsely-colored processing unit 133 as output of an image signal. However, the present invention does not have to be restricted to such a configuration.

For example, as shown in FIG. 22, it is possible to adopt a configuration that spectral characteristic ($O_{ij}(\lambda)$) of a subject is estimated from weighting factors ($w2_{ij}$, $w3_{ij}$) concerning general-purpose base vectors ($O2(\lambda)$, $O3(\lambda)$) in units of each pixel, the estimated spectral characteristic ($O_{ij}(\lambda)$) is corrected by using a weighting factor ($w1_{ij}$) concerning a dedicated base vector ($O1(\lambda)$), and a color image signal is generated from the corrected spectral characteristic ($O'_{ij}(\lambda)$).

FIG. 22 shows a conformation that the normalization unit 116 and the second normalization unit 132 are omitted from the configuration depicted in FIG. 20 and a spectral characteristic estimation unit 134, a correction unit 135 and a conversion unit 136 are added. A basic configuration is equivalent to that depicted in FIG. 20, and like names and like reference numeral denote like structures. Different points alone will be explained hereinafter.

A second calculation unit 131 is connected to the spectral characteristic estimation unit 134. A calculation unit 112 and a spectral characteristic estimation unit 134 are connected to the correction unit 135. The correction unit 135 is connected to a changeover unit 113 through the conversion unit 136. A system spectral characteristic ROM 115 is connected to the calculation unit 112, a second calculation unit 131 and the conversion unit 136. A control unit 118 is bi-directionally connected with the spectral characteristic estimation unit 134, the correction unit 135, and the conversion unit 136.

Weighting factors ($w2_{ij}$, $w3_{ij}$) concerning general-purpose base vectors ($O2(\lambda)$, $O3(\lambda)$) calculated by the second calculation unit 131 and the general-purpose base vectors ($O2(\lambda)$, $O3(\lambda)$) are transferred to the spectral characteristic estimation unit 134. The spectral characteristic estimation unit 134 estimates spectral characteristic ($O_{ij}(\lambda)$) of subjects in units of pixel based on the following expression (6) under control of the control unit 118.

$$O_{ij}(\lambda) = w2_{ij} \cdot O2(\lambda) + w3_{ij} \cdot O3(\lambda) \quad (6)$$

The spectral characteristic $O_{ij}(\lambda)$ of the subjects calculated in an entire visible range based on expression (6) is transferred to the correction unit 135.

On the other hand, as described above, the calculation unit 112 calculates a weighting factor ($w1_{ij}$) concerning a dedicated base vector ($O1(\lambda)$) and transfers it together with the dedicated base vector ($O1(\lambda)$) to the correction unit 135.

The correction unit 135 corrects the spectral characteristic ($O_{ij}(\lambda)$) of the subjects transferred from the spectral characteristic estimation unit 134 based on the weighting factor ($w1_{ij}$) transferred from the calculation unit 112 under control of the control unit 118. The weighting factor ($w1_{ij}$) has a value that is proportionate to presence of a subject as an identification target, e.g., oxyhemoglobin. Therefore, in a region of, e.g., a vessel where the weighting factor ($w1_{ij}$) is large, an accuracy of the spectral characteristic can be improved by substituting a spectral characteristic of an identification target itself for spectral characteristic calculated based on the general-purpose base vector shown in expression (6). The correction unit 135 mixes the spectral characteristic ($O_{ij}(\lambda)$) of the subjects with the spectral characteristic of the identification target itself based on the weighing factor ($w1_{ij}$) as represented by the following expression (7), thereby obtaining a corrected spectral characteristic ($O'_{ij}(\lambda)$). It is to be noted that, since the dedicated base vector ($O1(\lambda)$) is based on the spectral characteristic of the identification target itself as shown in FIG. 4, it can be diverted to the spectral characteristic of the identification target. Further, in the following expression (7), it is premised that the weighting factor ($w1_{ij}$) can take a value from "0" to "1".

$$O'_{ij}(\lambda) = w1_{ij} \cdot O1(\lambda) + (1 - w1_{ij}) \cdot O_{ij}(\lambda) \tag{7}$$

The correction unit 135 transfers to the conversion unit 136 the spectral characteristic ($O'_{ij}(\lambda)$) corrected based on expression (7) and the weighting factor ($w1_{ij}$) transferred from the calculation unit 112.

Figure 23:
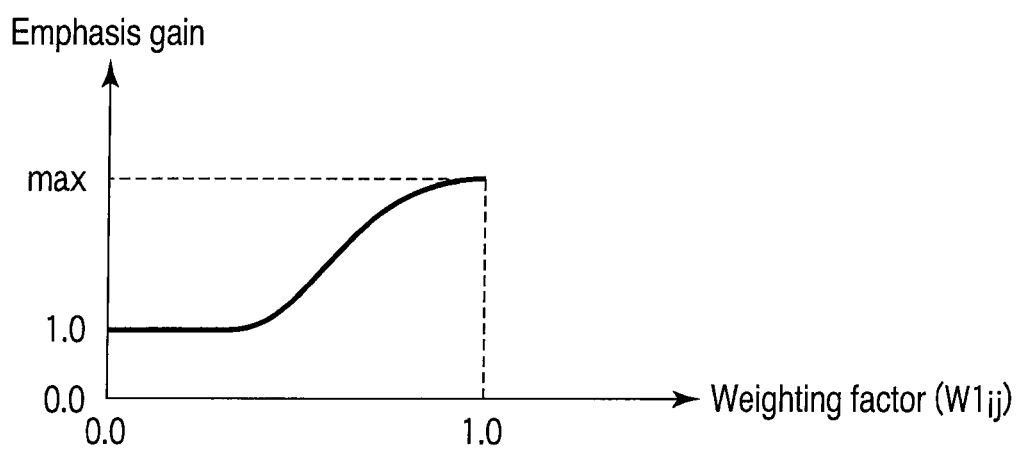
FIG. 23 is a view showing an emphasis gain generating function.

The conversion unit 136 reads such spectral characteristics ($SR(\lambda)$, $SG(\lambda)$, $SB(\lambda)$) concerning a color imaging system as shown in FIG. 6 from the system spectral characteristic ROM 115 under control of the control unit 118. Then, it calculates three signals $R_{ij}$, $G_{ij}$, and $B_{ij}$ based on the corrected spectral characteristic ($O'_{ij}(\lambda)$) transferred from the correction unit 135 by using the following expression (8).

$$R_{ij} = \text{gain}(W1_{ij}) \cdot k \cdot \sum_{\lambda=380,780} O'_{ij}(\lambda) \cdot SR(\lambda) \tag{8}$$

$$G_{ij} = k \cdot \sum_{\lambda=380,780} O'_{ij}(\lambda) \cdot SG(\lambda)$$

$$B_{ij} = k \cdot \sum_{\lambda=380,780} O'_{ij}(\lambda) \cdot SB(\lambda)$$

k in expression (8) means a correction coefficient configured to accord the three signals $R_{ij}$, $G_{ij}$, and $B_{ij}$ with a signal level of an image signal (e.g., "0" to "255" if a signal level consists of 8 bits). Further, gain ( ) is a function that generates a gain for emphasis processing and indicates, e.g., a characteristic shown in FIG. 23.

The conversion unit 136 transfers the three signals $R_{ij}$, $G_{ij}$, and $B_{ij}$ calculated based on expression (8) to the changeover unit 113 as a frame signal. The frame signal generated by this conversion unit 136 is a signal having R emphasized in proportion to presence of the identification target and having improved identification properties. Furthermore, in regard to a region where the subject as the identification target is not present, i.e., a region where a subject which is not the identification target is present, the signal is likewise generated by the equivalent processing, thereby obtaining an image signal having excellent uniformity and continuity with respect to the identification target and good visibility. In this manner, the spectral characteristic estimation unit 134, the correction unit 135, the conversion unit 136, the changeover unit 113, and the output unit 117 function as an output signal calculation unit that calculates an output signal as an identification result of the subject which is the identification target based on the weighting factor concerning the dedicated base vector, for example.

As described above, in this Modification 1, spectral characteristic of the subjects in the entire screen is estimated from the general-purpose base vector used for estimating a spectral characteristic of an arbitrary subject, correction is performed in regard to a subject as the identification target alone by using the weighting factor concerning the dedicated base vector, and an output signal is calculated from the corrected spectral characteristic. Therefore, since the spectral characteristic of the subjects in the entire screen is obtained from the general-purpose base vector and the dedicated base vector to calculate the output signal, continuity of a region of the identification target and any other region can be maintained, and the output signal having good visibility can be obtained. Moreover, since the correction is performed in regard to the identification target by using the dedicated base vector, an error in estimation of the spectral characteristics can be suppressed, thus enabling accurate identification.

It is to be noted that, in this modification, likewise, the calculation unit 112 and the second calculation unit 131 may use the dedicated base vectors alone for all subjects or may use the dedicated base vector of at least the subject as the identification target and the general-purpose base vectors for other subjects. Additionally, a total number of the base vectors is not restricted to three as described above. Further, the calculation unit 112 and the second calculation unit 131 may be integrated as one calculation unit. Furthermore, this configuration can be of course applied to both a video image and a still image.

As described above, when the spectral characteristic of the subjects in the entire screen is obtained from the dedicated base vectors of the subject as the identification target and subjects which are not the identification target to calculate the output signal, the continuity of the region of the identification target and any other region can be maintained, and the output signal having good visibility can be obtained. Moreover, since the correction is carried out in regard to the identification target by using the dedicated base vector of the subject as the identification target, an error in estimation of the spectral characteristics can be suppressed, and accurate identification can be performed.

[Modification 2]

Further, the processing using hardware is premised in the second embodiment, but the present invention does not have to be restricted to such a configuration. For example, it is possible to adopt a configuration that an image signal from the CCD 101 takes a Raw data format without being subjected to processing, an image acquisition condition such as a subject as an identification target, the color imaging system, illumination light, and others is output as header information from the control unit 118, and the image signal and the header information are input to a non-illustrated computer to be processed by software.

Figure 24:
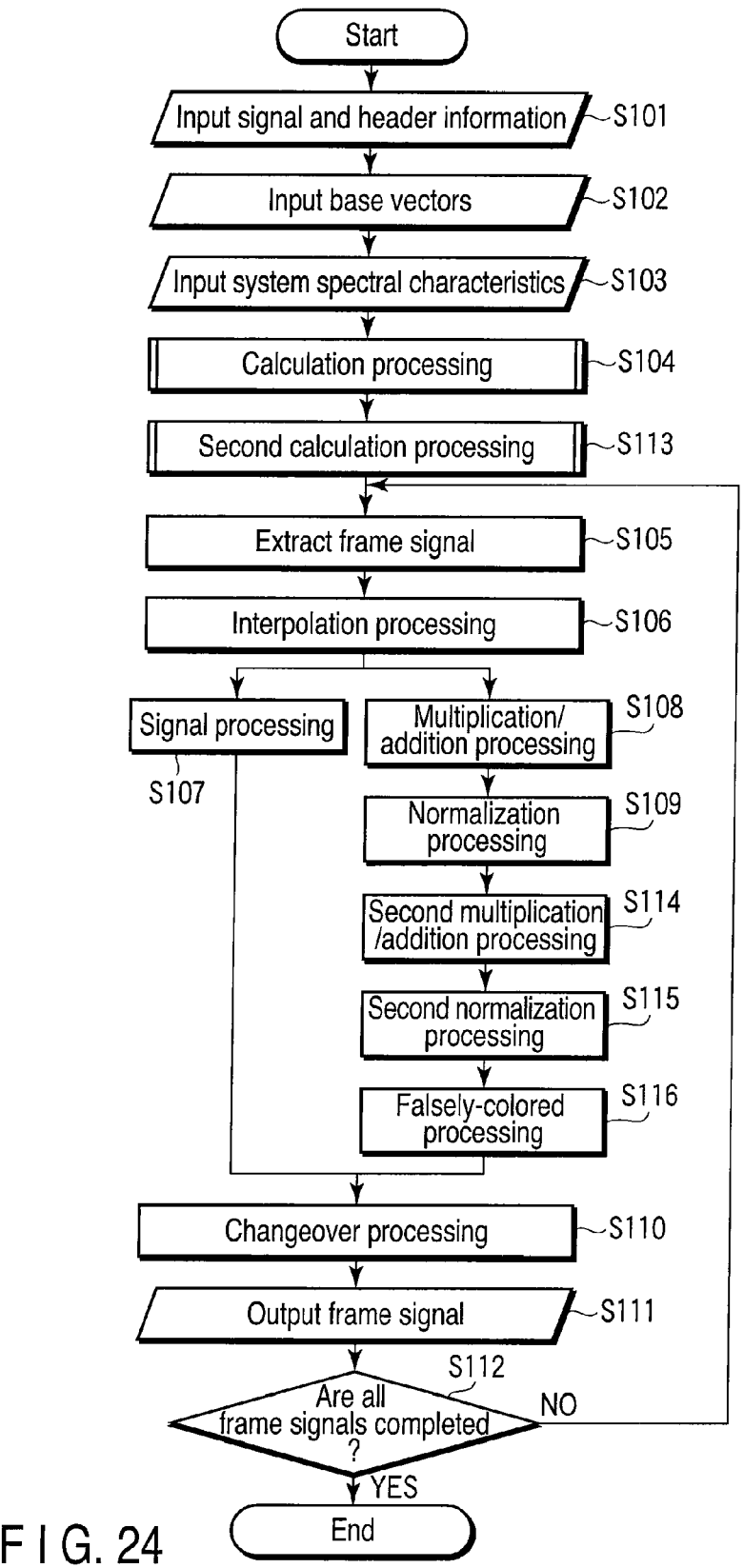
FIG. 24 is a view showing a flowchart concerning software processing of signal processing in Modification 2 of the second embodiment.

FIG. 24 is a view showing a flowchart concerning software processing of signal processing using a non-illustrated computer. It is to be noted that like reference numerals denote processing steps equal to those in the flowchart of the signal processing in the first embodiment depicted in FIG. 18.

That is, the computer first receives an image signal and header information concerning an image acquisition condition such as an identification target or a subject, the color imaging system, illumination light, and others (step S101). It is to be noted that processing an image signal from a Bayer type single CCD including three color filters 121R, 121G, and 121B is assumed in this modification.

Then, a plurality of dedicated base vectors and a plurality of general-purpose base vectors are input (step S102), and a plurality of light source spectral luminance characteristics and a plurality of color imaging system spectral sensitivity characteristics are input (step S103). Here, the plurality of base vectors and the plurality of spectral characteristics are input by being read out from a recording medium provided in the computer or a detachable recording medium or being read out through a network.

Furthermore, based on such calculation processing as described in conjunction with FIG. 19, predetermined coefficients of an inverse matrix $M^{-1}$ of a system matrix M used for calculating a weighting factor concerning a dedicated base vector ($O1(\lambda)$), i.e., elements $m_{11}$, $m_{12}$, and $m_{13}$ are calculated (step S104). Moreover, based on second calculation processing which will be described later in detail, coefficients of the inverse matrix $M^{-1}$ of the system matrix M used for calculating weighting factors concerning general-purpose base vectors $(O2(\lambda), O3(\lambda))$, i.e., elements $m_{21}$, $m_{22}$, $m_{23}$, $m_{31}$, $m_{32}$, and $m_{33}$ are calculated (step S113).

Thereafter, frame signals are sequentially extracted from the input image signals (step S105), and three color frame signals are generated by known interpolation processing (step S106). Moreover, signal processing such as known gradation processing or emphasis processing is carried out with respect to these frame signals (step 107).

Additionally, a weighting factor $(w1_{ij})$ concerning the dedicated base vector $(O1(\lambda))$ is calculated as represented by expression (3) simultaneously with the signal processing at the step S107 (step S108), and a frame signal concerning presence of an identification target is generated by normalizing the calculated weighting factor $(w1_{ij})$ (step S109). Further, weighting factors $(w2_{ij}, w3_{ij})$ concerning such general-purpose base vectors $(O2(\lambda), O3(\lambda))$ as shown in expression (4) and expression (5) are calculated (step S114), and a frame signal concerning a region where the subject as the identification target is not present, i.e., a region where a subject other than the identification target is present is generated by normalizing the calculated weighting factors $(w2_{11}, w3_{ij})$ (step 115). Further, falsely-colored processing is carried out from the frame signal concerning the presence of the identification target generated at the step S109 and the frame signal concerning the region where a subject other than the identification target is present generated at the step S115 (step 116).

Furthermore, one of the ordinary frame signal obtained at the step S107 and the frame signal subjected to the falsely-colored processing at the step S116 is changed over (step S110), and the frame signal is output to a non-illustrated display monitor or the like connected to the computer (step S111). Then, whether all frame signals are completed is judged (step S112), and the processing returns to the step S105 when they are not completed, or the processing is terminated when they are completed.

The second calculation processing at the step S113 is carried out as shown in FIG. 25.

First, data to be used is selected from the plurality of dedicated base vectors and the plurality of general-purpose base vectors input at the step S102 and the plurality of light source spectral luminance characteristics and the plurality of color imaging system spectral sensitivity characteristics input at the step S103 (step S211). This operation selects dedicated base vector, general-purpose base vectors, light source spectral luminance characteristic, and color imaging system spectral sensitivity characteristics based on an image acquisition condition such as a subject which is an identification target, the color imaging system, illumination light, and others in the header information input at the step S101. For example, the operation selects such a dedicated base vector $(O1(\lambda))$ and general-purpose base vectors $(O2(\lambda), O3(\lambda)$ as shown in FIG. 7, such spectral luminance characteristic of the light source as shown in FIG. 5, and such spectral sensitivity characteristics of the color imaging system as shown in FIG. 6.

Thereafter, the system matrix M represented by expression (1) is calculated (step S212), and the inverse matrix $M^{-1}$ of the system matrix M is further calculated (step S213). Furthermore, the elements $m_{21}$, $m_{22}$, $m_{23}$, $m_{31}$, $m_{32}$, and $m_{33}$ of the inverse matrix $M^{-1}$ required for calculating the weighting factors $(w2_{ij}, w3_{ij})$ of the general-purpose base vectors $(O2(\lambda), O3(\lambda)$ are selected as the predetermined coefficients (step S214), and the selected elements $m_{21}$, $m_{22}$, $m_{23}$, $m_{31}$, $m_{32}$, and $m_{33}$ of the inverse matrix $M^{-1}$ are output (step S215).

It is to be noted that the example where the processing associated with the second embodiment is carried out by software has been described here, and it is needless to say that processing like the Modification 1 can be likewise carried out by software.

Moreover, although the example where the one dedicated base vector and the two general-purpose base vectors are utilized in the second calculation processing has been described, three dedicated base vectors may be used, or two dedicated base vectors and one general-purpose base vector may be used. Additionally, the total number of the base vectors is not restricted to three as described above. In the calculation processing, if at least the dedicated base vector of the subject as the identification target is likewise used, dedicate base vectors or general-purpose vase vectors may be used as remaining vectors.

Further, since the calculation processing and the second calculation processing are basically equivalent to each other, they can be of course integrated to calculate all weighting factors concerning dedicated base vectors and general-purpose base vectors by single calculation processing. Furthermore, this configuration can be of course applied to both a video image and a still image.

Third Embodiment

A third embodiment according to the present invention will now be described.

(Configuration)

As shown in FIG. 26, a microscope to which a signal processing system according to a third embodiment of the present invention is applied has a configuration that the calculation unit 112, the base vector ROM 114, and the system spectral characteristic ROM 115 are omitted from the configuration according to the first embodiment depicted in FIG. 1 and a correlation coefficient calculation unit 137 and a derivation coefficient ROM 138 are added. A basic configuration is equivalent to that of the first embodiment, and like names and like, reference numerals denote like structures. Different points alone will be described hereinafter.

In this embodiment, an image signal from a CCD 101 in an endoscope is amplified by an amplification unit 105 and converted into a digital signal by an analog-to-digital converter 106. Illumination light from an illumination light source 103 is led to an object stage of the microscope through an illumination lens system 102. An interpolation unit 108 is connected to a signal processing unit 111 and the correlation coefficient, calculation unit 137. The derivation coefficient ROM 138 is connected to the correlation coefficient calculation unit 137. The correlation coefficient calculation unit 137 is connected to a normalization unit 116. A control unit 118 is bi-directionally connected with the correlation coefficient calculation unit 137.

(Function)

A function of the signal processing system according to this embodiment is basically equivalent to that of the first embodiment, and different points alone will be described.

In FIG. 26, a flow of signals will be explained. After an image acquisition condition such as a subject which is a later-described identification target have been set through an external interface unit 119, the microscope is entered a pre-image acquisition mode by partly pressing a non-illustrated shutter button in the external interface unit 119. The CCD 101 acquires a subject image formed on the CD 101 through an imaging lens system 100 and outputs an image signal as an analog signal. The analog signal is amplified by a predetermined amount in the amplification unit 105 and converted into a digital signal by the analog-to-digital converter 106 to be transferred to a buffer 107. The image signal in the buffer 107 is transferred to a WB unit 109 and a photometric evaluation unit 110 under control of the control unit 118. Like the first embodiment, the WB unit 109 executes white balance processing, and the photometric evaluation unit 110 carries out exposure control.

Then, actual image acquisition is performed by fully pressing the shutter button in the external interface unit 119, and the image signal is transferred to the buffer 107 like the pre-image acquisition. The image signal in the buffer 107 is transferred to the interpolation unit 108. The interpolation unit 108 reads the three-color image signal from the buffer 107 and generates three color image signals based on known interpolation processing under control of the control unit 118. The generated three color image signals are transferred to the signal processing unit 111 and the correlation coefficient calculation unit 137.

The signal processing unit 111 executes known gradation processing and emphasis processing with respect to the image signals transferred from the interpolation unit 108 and transfers the processed image signal to the changeover unit 113 under control of the control unit 118.

On the other hand, the derivation coefficient ROM 138 stores derivation coefficients that are utilized to derive a correlation between a spectral characteristic of each subject as an identification target and an image signal in accordance with each subject. These derivation coefficients are previously calculated based on a known spectral characteristic of the subject, spectral characteristic concerning the color imaging system used for image acquisition of the subjects, and spectral characteristic concerning illumination light used for image acquisition of the subjects, and are stored. In this manner, the derivation coefficient ROM 138 functions as, e.g., a derivation coefficient acquisition unit that acquires derivation coefficients indicative of a correlation between a known spectral characteristic of a subject and an image signal. The correlation calculation unit 137 selectively reads the derivation coefficients from the derivation coefficient ROM 138 under control of the control unit 118 associated with selection of a subject as an identification target based on the image acquisition condition set through the external interface unit 119. Then, this unit calculates a correlation coefficient between the spectral characteristic of the subject as the identification target and the image signal with respect to the image signals transferred from the interpolation unit 108 by using the read derivation coefficients. The correlation coefficient calculated by this correlation coefficient calculation unit 137 takes a value that is proportionate to presence of the subject as the identification target, and it is transferred to the normalization unit 116 to be normalized so that it can coincide with a signal level of the image signal (e.g., "0" to "255" if the signal level consists of 8 bits). The normalized correlation coefficient is transferred to the changeover unit 113 as an image signal.

The changeover unit 113 selects one of the ordinary image signal transferred from the signal processing unit 111 and the image signal concerning presence of the identification target that is transferred from the normalization unit 116 and transfers the selected signal to the output unit 117 which is, e.g., a display monitor under control of the control unit 118. It is to be noted that the image signal from the normalization unit 116 is output as a monochrome signal. Further, the output unit 117 is not restricted to the display monitor, and a conformation that each image signal is recorded and stored in a recording medium such as a hard disk or a memory card can be adopted. In this manner, the changeover unit 113, the normalization unit 116, and the output unit 117 function as, e.g., an output signal calculation unit that calculates an output signal as an identification result of a subject as an identification target based on a correlation coefficient calculated by the correlation coefficient calculation unit 137.

As shown in FIG. 27, the correlation coefficient calculation unit 137 is constituted of a coefficient selection unit 227 and a multiplication/addition unit 226. Here, the derivation coefficient ROM 138 is connected to the multiplication/addition unit 226 through the coefficient selection unit 227. The interpolation unit 108 is connected to the multiplication/addition unit 226. The multiplication/addition unit 226 is connected to the normalization unit 116. The control unit 118 is bi-directionally connected with the coefficient selection unit 227 and the multiplication/addition unit 226.

The coefficient selection unit 227 receives from the control unit 118 information of a subject as an identification target under the image acquisition condition set through the external interface unit 119 and reads derivation coefficients that are utilized to derive a correlation between a spectral characteristic of the subject as the identification target and an image signal from the derivation coefficient ROM 138 based on the information. The derivation coefficient ROM 138 records each element of an inverse matrix $M^{-1}$ of a system matrix M represented by expression (2) as a derivation coefficient. This configuration has a premise that spectral characteristic concerning a color imaging system used for image acquisition of a subject and spectral characteristic concerning illumination light used for image acquisition of the subject by the color imaging system are fixed in the microscope. In this case, calculation processes represented by expression (1) and expression (2) can be omitted, and recording the finally obtained inverse matrix $M^{-1}$ of the system matrix M can suffice.

It is to be rioted that assumed types of dedicated base vectors based on known spectral characteristics of assumed subjects as an identification target are prepared and inverse matrixes $M^{-1}$ of a plurality of system matrixes are recorded. Here, it is assumed that $m_{11}$, $m_{12}$, and $m_{13}$ are read as derivation coefficients like the first embodiment. The derivation coefficients are transferred to the multiplication/addition unit 226.

The multiplication/addition unit 226 reads the derivation coefficients from the coefficient selection unit 227 and the image signals from the interpolation unit 108 in units of pixel under control of the control unit 118. Then, based on expression (3), each weighting factor is obtained. The weighting factor serves as a correlation coefficient indicative of a correlation between a known spectral characteristic of the subject as the identification target and the image signal. This correlation coefficient is sequentially transferred to the normalization unit 116.

As described above, according to this third embodiment, the correlation coefficient between the known spectral characteristic of the subject as the identification target and the image signal that takes a value proportional to presence of the subject as the identification target is obtained from the derivation coefficients based on the known spectral characteristic of the subject as the identification target, and an output signal which is an identification result of the subject as the identification target is calculated based on this correlation coefficient. As described above, according to the third embodiment, since the correlation coefficient, that takes a value proportional to presence of the subject as the identification target can be calculated by using the derivation coefficients based on the known spectral characteristic of the subject as the identification target, signal processing including an error like approximation based on the conventional least-square method does not have to be executed, and hence an error due to the signal processing hardly occurs, thereby enabling reliable identification.

Furthermore, since usual broadband illumination light is used, an influence of noise can be suppressed, and stable identification can be carried out. Moreover, calculating the correlation coefficient from the derivation coefficients is easy, and the output signal is directly calculated from the correlation coefficient, thereby achieving an increase in speed of the processing and a reduction in cost.

Additionally, since the output signal is obtained by normalizing the correlation coefficient concerning the derivation coefficients, the accurate output signal can be acquired in regard to presence of the identification target. Further, since the output signal is obtained by the normalization processing alone, an increase in speed of the processing and a reduction in cost can be achieved.

It is to be noted that still image processing using the microscope is executed in the description of the third embodiment, but the present invention does not have to be restricted to such a configuration. This configuration can be also applied to video image processing of an endoscope and others like those in the first and second embodiments as long as a spectral characteristic concerning the color imaging system and a spectral characteristic concerning the illumination light used for image acquisition of the subject are fixed.

Furthermore, an image signal acquired by a different image acquisition unit can take a Raw data format without being processed, and it is possible to acquire from a recording medium having the accompanying information concerning image acquisition condition of a subject as an identification target and others recorded in a header portion the image signal and accompanying information to be processed. Moreover, as explained in Modification 2 of the first embodiment, this configuration can be applied to the imaging system including the four primary color filters 122 or the color-difference line sequential type complementary filter 123 or to two CCDs or three CCDs.

[Modification 1]

Additionally, the third embodiment has the configuration that the changeover unit 113 selects and outputs one of an ordinary image signal transferred from the signal processing unit 111 and an image signal concerning presence of an identification target transferred from the normalization unit 116 as output of the image signal. However, the present invention does not have to be restricted to such a configuration.

For example, as shown in FIG. 28, the normalization unit 116 may be omitted from the configuration depicted in FIG. 26, and the emphasis unit 124 may substitute for the changeover unit 113. A basic configuration is equivalent to that shown in FIG. 26, and like names and like reference numerals denote like structures. Different points alone will be described hereinafter.

A signal processing unit 111 and a correlation coefficient calculation unit 137 are connected to the emphasis unit 124. The emphasis unit 124 is connected to an output unit 117. A control unit 118 is bi-directionally connected with the emphasis unit 124. To the emphasis unit 124 are transferred an ordinary image signal from the signal processing unit 111 and a correlation coefficient between a known spectral characteristic of a subject as an identification target and an image signal from the correlation coefficient calculation unit 137.

In such a configuration, the emphasis unit 124 emphasizes the image signal transferred from the signal processing unit 111 based on the correlation coefficient transferred from the correlation coefficient calculation unit 137 under control of the control unit 118. As the emphasis processing, known edge emphasis processing or chrome emphasis processing are assumed, and an emphasis amount of such processing is carried out to be proportionate to the correlation coefficient. The emphasized image signal is transferred to the output unit 117. In this manner, the emphasis unit 124 and the output unit 117 function as, e.g., an output signal calculation unit that calculates an output signal as an identification result of a subject which is an identification target based on the correlation coefficient calculated by the correlation coefficient calculation unit 137.

As described above, when the image signal subjected to the ordinary processing based on the correlation coefficient concerning the derivation coefficients is emphasized and output as an output signal, a region of a subject which is an identification target such as oxyhemoglobin is present alone is emphasized, thereby improving a recognition ability. Further, in regard to a region where the subject as the identification target is not present, i.e., a region where a subject other than the identification target is present, an image signal subjected to the ordinary processing is output, recognition of overall image signals can be facilitated, thereby improving operability for a user.

[Modification 2]

Furthermore, as shown in FIG. 29, a combination unit 125 may substitute for the changeover unit 113 in the configuration depicted in FIG. 26. A basic configuration is equivalent to that depicted in FIG. 26, and like names and like reference numerals denote like structures. Different points alone will be described hereinafter.

A signal processing unit 111 and a normalization unit 116 are connected to the combination unit 125. The combination unit 125 is connected to an output unit 117. A control unit 118 is bi-directionally connected with the combination unit 125. To the combination unit 125 are transferred an ordinary image signal transferred from the signal processing unit 111 and an image signal concerning presence of an identification target from the normalization unit 116.

In such a configuration, the combination unit 125 combines the image signal transferred from the signal processing unit 111 with the image signal concerning presence of an identification target transferred from the normalization unit 116 under control of the control unit 118. As the combination processing, processing such as known superimposition is assumed. The combined image signal is transferred to an output unit 117. In this manner, the normalization unit 116, the combination unit 125, and the output unit 117 function as, e.g., an output signal calculation unit that calculates an output signal as an identification result of a subject which is an identification target based on a correlation coefficient calculated by a correlation coefficient calculation unit 137.

As described above, when the image signal concerning the identification target is obtained by normalizing the correlation coefficient concerning derivation coefficients, an accurate image signal can be obtained in relation to a region where the subject as the identification target is present. Moreover, since the image signals subjected to the ordinary processing are combined with each other, the image signal subjected to the ordinary processing is output in regard to a region where the subject as the identification target is not present, i.e., a region where a subject other than the identification target is present, and recognition of overall image signals is facilitated, thereby improving operability for a user.

Additionally, the combination unit 125 may execute combination processing such as known picture-in-picture that is configured to display a window in a part of a screen and show an image signal from the signal processing unit 111 or an image signal from the normalization unit 116 as a child screen. In this case, it is preferable to enable selecting a parent screen and a child screen based on an instruction supplied through an external interface unit 119.

[Modification 3]

Figure 30:
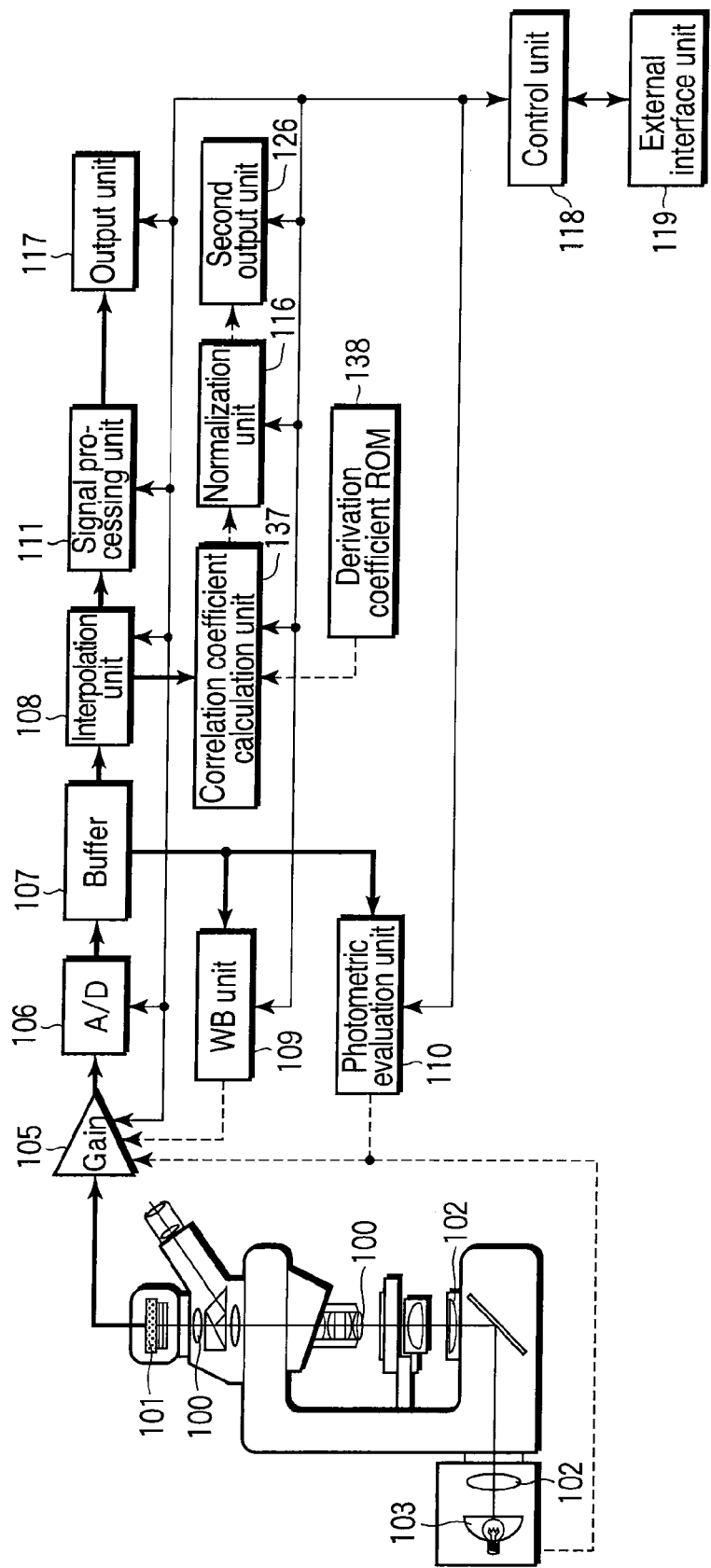
FIG. 30 is a view showing a configuration of an endoscope to which a signal processing system according to Modification 3 of the third embodiment is applied.

Further, as shown in FIG. 30, the changeover unit 113 may be omitted from the configuration depicted in FIG. 26 and a second output unit 126 may be added. A basic configuration is equivalent to that depicted in FIG. 26, and like names and like reference numerals denote like structures. Different points alone will be described hereinafter.

A signal processing unit 111 is connected to an output unit 117. A normalization unit 116 is connected to the second output unit 126. A control unit 118 is bi-directionally connected with the second output unit 126. The signal processing unit 111 transfers an ordinary image signal to the output unit 117 under control of the control unit 118. In the output unit 117, the ordinary image signal is displayed. The normalization unit 116 transfers an image signal concerning presence of an identification target to the second output unit 126 under control of the control unit 118. In the second output unit 126, the image signal concerning presence of the identification target is displayed. In this manner, the normalization unit 116, the output unit 117, and the second output unit 126 function as, e.g., an output signal calculation unit that calculates an output signal as an identification result of a subject which is the identification target based on a correlation coefficient calculated by a correlation coefficient calculation unit 137.

As described above, when the image signal concerning the identification target is obtained by normalizing the correlation coefficient concerning derivation coefficients, an accurate output signal can be obtained in relation to presence of the identification target. Further, since the image signal subjected to the ordinary processing is also independently output, recognition of overall image signals can be facilitated, thereby improving operability for a user.

[Modification 4]

Furthermore, although the processing using hardware is a presupposition in the third embodiment, the present invention does net have to be restricted to such a configuration. For example, an image signal from a CCD 101 may have a Raw data format without being processed, image acquisition condition such as subject as an identification target may be output as header information from the control unit 118, and the image signal and the header information may be input, to a non-illustrated computer to be processed by software.

Figure 31:
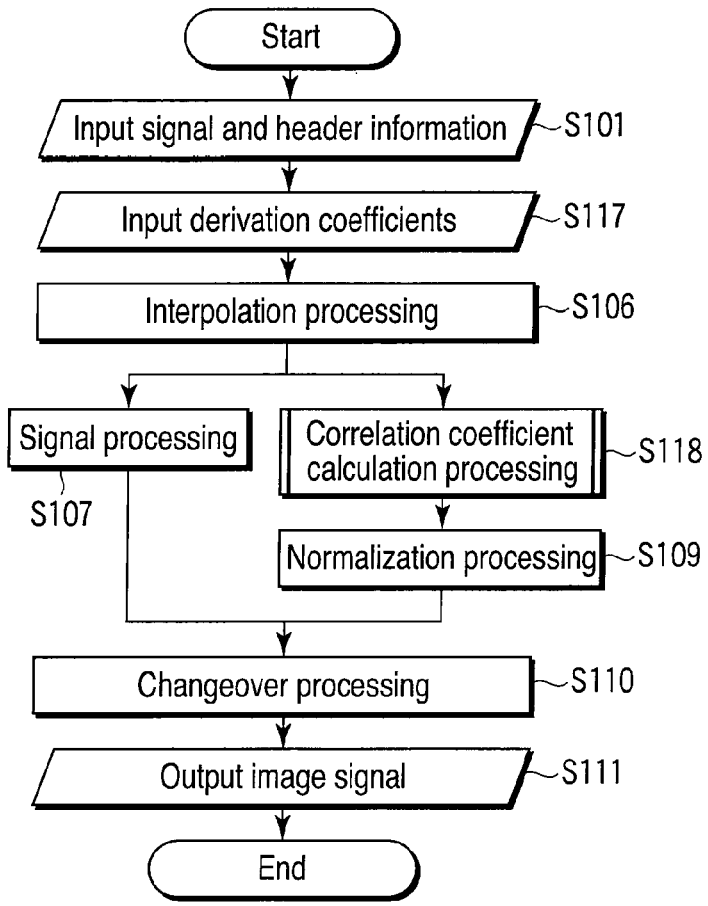
FIG. 31 is a view showing a flowchart concerning software processing of signal processing in Modification 4 of the third embodiment.

FIG. 31 is a view showing a flowchart concerning software processing of signal processing executed by the non-illustrated computer. It is to be noted that like reference numerals denote processing steps equal to those in the flowchart of the signal processing in the first embodiment depicted in FIG. 1.

That is, the computer first receives an image signal and header information concerning an image acquisition condition such as a subject which is an identification target (step S101) and also receives a plurality of derivation coefficients (step S117). Here, the derivation coefficients are input by being read out from a recording medium included in the computer or a detachable recording medium or by being read out through a network.

Moreover, three color image signals are generated from the input image signal by known interpolation processing (step S106), and signal processing such as known gradation processing or emphasis processing is carried out with respect to this image signal (step S107).

Additionally, a correlation coefficient between the known spectral characteristic of the subject as the identification target and the image signal are calculated based on the input derivation coefficients by correlation coefficient calculation processing which will be described later in detail simultaneously with the signal processing at the step S107 (step S118). Further, an image signal concerning presence of the identification target is generated by normalizing the correlation coefficient (step S109).

Furthermore, one of the ordinary image signal obtained at the step S107 and the image signal concerning presence of the subject as the identification target obtained at the step S109 is changed over (step S110), and the image signal is output to, e.g., a non-illustrated display monitor connected with the computer (step S111), thereby terminating the processing.

Figure 18:
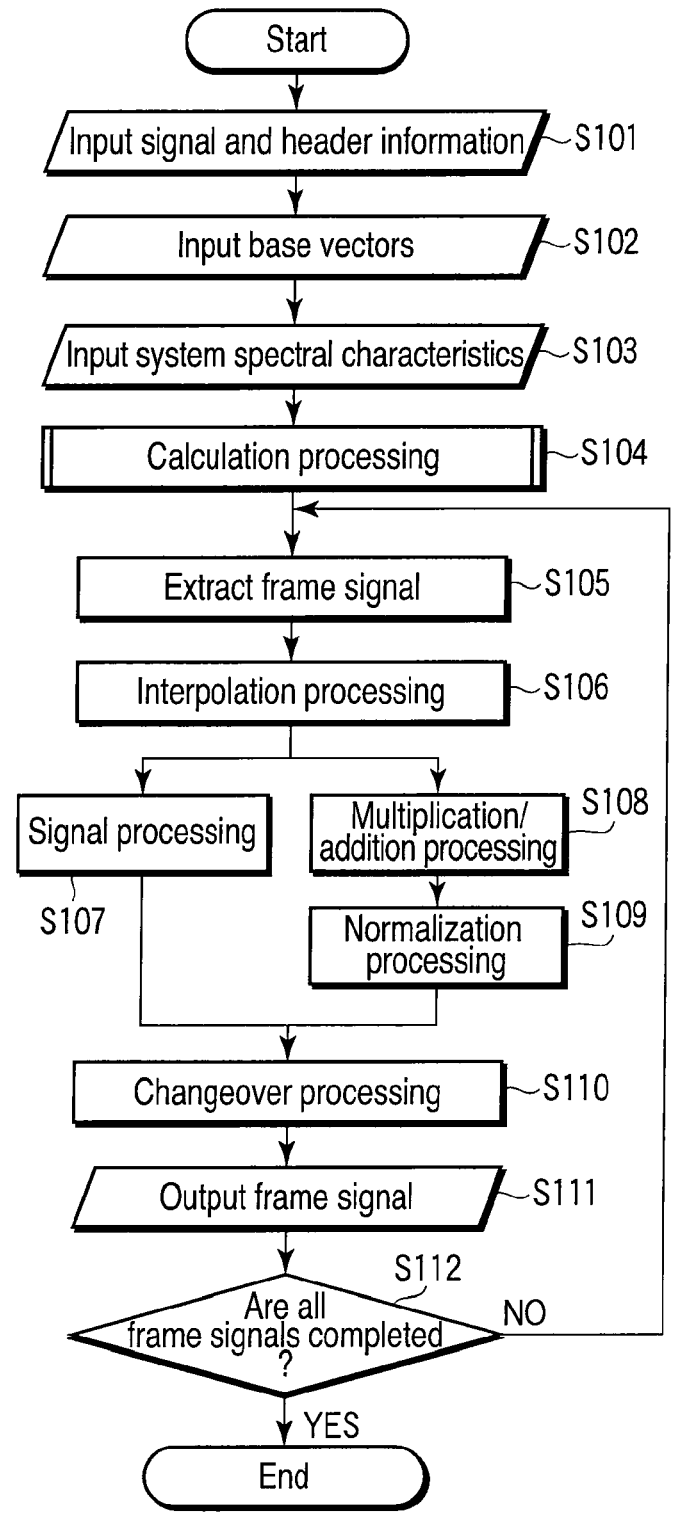
FIG. 18 is a view showing a flowchart concerning software processing of signal processing in Modification 7 of the first embodiment.

It is to be noted that, in case of a microscope, a still image rather than a video image is processed, and hence such a judgment on whether all frame signals have been completed as shown in FIG. 18 or FIG. 24 is not required.

Figure 32:
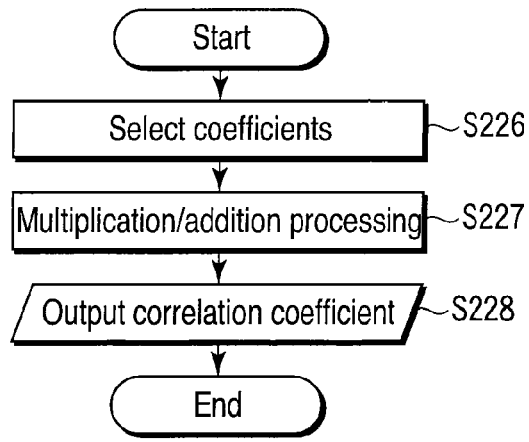
FIG. 32 is a view showing a flowchart concerning correlation coefficient calculation processing in FIG. 31.

The correlation coefficient calculation processing at the step S118 is carried out as shown in FIG. 32.

First, derivation coefficients are selected from the plurality of derivation coefficients input at the step S117 based on information of the subject as the identification target in the header information input at the step S101 (step S226). Moreover, as represented by expression (3), a correlation coefficient is calculated based on the derivation coefficients (step S227), and the calculated correlation coefficient is output (step S228).

It is to be noted that the example where the processing corresponding to the third embodiment is carried out by software has been described here, but the processing like Modifications 1 to 4 may be course likewise carried out by software.

Additional advantages and modifications will readily occur to those skilled in the art. Therefore, the invention in its broader aspects is not limited to the specific details, and representative devices shown and described herein. Accordingly, various modifications may be made without departing from the spirit, or scope of the general inventive concept as defined by the appended claims and their equivalents.

What is claimed is:

1. A signal processing system comprising:
a base vector acquisition unit configured to acquire (i) a dedicated base vector based on a known spectral characteristic of a subject as an identification target having the known spectral characteristic, the known spectral characteristic being a spectral reflectance characteristic for wavelengths including wavelengths of a visible range, and (ii) a general-purpose base vector together with the dedicated base vector, the general-purpose base vector being used in estimation of a spectral characteristic of an arbitrary subject;
a system spectral characteristic acquisition unit configured to acquire a spectral characteristic of an imaging system including a spectral characteristic concerning a color imaging system used for image acquisition of subjects including the subject as the identification target and a spectral characteristic concerning illumination light used for image acquisition of the subjects by the color imaging system;
a calculation unit configured to calculate (i) a weighting factor concerning the dedicated base vector using an image signal, the dedicated base vector, and the spectral characteristic of the imaging system, and (ii) a weighting factor concerning the general-purpose base vector using the image signal, the general-purpose base vector, the dedicated base vector, and the spectral characteristic of the imaging system; and
an output signal calculation unit configured to calculate an output signal as an identification result of the subject which is the identification target based on the weighting factor concerning the dedicated base vector and the weighting factor concerning the general-purpose base vector calculated by the calculation unit.

2. The system according to claim 1, wherein the base vector acquisition unit further acquires a dedicated base vector based on a known spectral characteristic of a subject which is not the identification target and which has a known spectral characteristic different from the known spectral characteristic of the subject as the identification target in addition to the dedicated base vector based on the known spectral characteristic of the subject as the identification target.

3. The system according to claim 2, wherein the calculation unit comprises:
   a matrix calculation unit configured to calculate a system matrix concerning the imaging system on the basis of the dedicated base vector based on the known spectral characteristic of the subject as the identification target, the dedicated base vector based on the known spectral characteristic of the subject which is not the identification target, and the general-purpose base vector which are acquired by the base vector acquisition unit and the spectral characteristic of the imaging system acquired by the system spectral characteristic acquisition unit;
   an inverse matrix calculation unit configured to calculate an inverse matrix of the system matrix calculated by the matrix calculation unit;
   a coefficient selection unit configured to select coefficients concerning the dedicated base vector based on the known spectral characteristic of the subject as the identification target from coefficients of the inverse matrix calculated by the inverse matrix calculation unit; and
   a multiplication/addition unit configured to calculate a weighting factor concerning the dedicated base vector based on the known spectral characteristic of the subject as the identification target on the basis of the coefficients selected by the coefficient selection unit and the image signal from the color imaging system.

4. The system according to claim 2, wherein:
   the calculation unit further calculates a weighting factor concerning the dedicated base vector based on the known spectral characteristic of the subject which is not the identification target on the basis of the image signal, the dedicated base vector based on the known spectral characteristic of the subject as the identification target, the dedicated base vector based on the known spectral characteristic of the subject which is not the identification target, and the general-purpose base vector acquired by the base vector acquisition unit, and the spectral characteristic of the imaging system acquired by the system spectral characteristic acquisition unit; and
   the output signal calculation unit calculates the output signal on the basis of the weighting factor concerning the dedicated base vector based on the known spectral characteristic of the subject as the identification target, the weighting factor concerning the dedicated base vector based on the known spectral characteristic of the subject which is not the identification target, and the weighting factor concerning the general-purpose base vector calculated by the calculation unit.

5. The system according to claim 4, wherein the output signal calculation unit comprises:
   a normalization unit configured to normalize the weighting factor concerning the dedicated base vector based on the known spectral characteristic of the subject as the identification target, the weighting factor concerning the dedicated base vector based on the known spectral characteristic of the subject which is not the identification target, and the weighting factor concerning the general-purpose base vector calculated by the calculation unit; and
   a falsely-colored processing signal calculation unit configured to calculate a false color signal as the output signal from the weighting factor concerning the dedicated base vector based on the known spectral characteristic of the subject as the identification target, the weighting factor concerning the dedicated base vector based on the known spectral characteristic of the subject which is not the identification target, and the weighting factor concerning the general-purpose base vector that are normalized by the normalization unit.

6. The system according to claim 4, wherein the output signal calculation unit comprises:
   a spectral characteristic estimation unit configured to estimate a spectral characteristic of a subject based on the weighting factor concerning the dedicated base vector based on the known spectral characteristic of the subject which is not the identification target and the weighting factor concerning the general-purpose base vector calculated by the calculation unit;
   a correction unit configured to correct the spectral characteristic estimated by the spectral characteristic estimation unit based on the weighting factor concerning the dedicated base vector based on the known spectral characteristic of the subject as the identification target calculated by the calculation unit; and
   a conversion unit configured to calculate the output signal based on the spectral characteristic corrected by the correction unit.

7. The system according to claim 4, wherein the calculation unit comprises:
   a matrix calculation unit configured to calculate a system matrix concerning the imaging system on the basis of the dedicated base vector based on the known spectral characteristic of the subject as the identification target, the dedicated base vector based on the known spectral characteristic of the subject which is not the identification target, and the general-purpose base vector that are acquired by the base vector acquisition unit and the spectral characteristic of the imaging system acquired by the system spectral characteristic acquisition unit;
   an inverse matrix calculation unit configured to calculate an inverse matrix of the system matrix calculated by the matrix calculation unit;
   a coefficient selection unit configured to select coefficients concerning the dedicated base vector based on the known spectral characteristic of the subject which is not the identification target from coefficients of the inverse matrix calculated by the inverse matrix calculation unit; and
   a multiplication/addition unit configured to calculate a weighting factor concerning the dedicated base vector based on the known spectral characteristic of the subject other than the identification target on the basis of the coefficient selected by the coefficient selection unit and the image signal from the color imaging system.

8. The system according to claim 1, wherein the calculation unit comprises:
   a matrix calculation unit configured to calculate a system matrix concerning the imaging system based on the general-purpose base vector and the dedicated base vector acquired by the base vector acquisition unit and the spectral characteristic of the imaging system acquired by the system spectral characteristic acquisition unit;

an inverse matrix calculation unit configured to calculate an inverse matrix of the system matrix calculated by the matrix calculation unit;

a coefficient selection unit configured to select coefficients concerning the dedicated base vector from coefficients of the inverse matrix calculated by the inverse matrix calculation unit; and a multiplication/addition unit configured to calculate a weighting factor concerning the dedicated base vector based on the coefficients selected by the coefficient selection unit and the image signal from the color imaging system.

9. The system according to claim 1, wherein the output signal calculation unit comprises:

a normalization unit configured to normalize the weighting factor concerning the dedicated base vector and the weighting factor concerning the general-purpose base vector calculated by the calculation unit; and a falsely-colored processing signal calculation unit configured to calculate a false color signal as the output signal from the weighting factor concerning the dedicated base vector and the weighting factor concerning the general-purpose base vector which are normalized by the normalization unit.

10. The system according to claim 1, wherein the output signal calculation unit comprises:

a spectral characteristic estimation unit configured to estimate a spectral characteristic of a subject based on the weighting factor concerning the general-purpose base vector calculated by the calculation unit;

a correction unit configured to correct the spectral characteristic estimated by the spectral characteristic estimation unit based on the weighting factor concerning the dedicated base vector calculated by the calculation unit; and a conversion unit configured to calculate the output signal based on the spectral characteristic corrected by the correction unit.

11. The system according to claim 1, wherein the calculation unit comprises:

a matrix calculation unit configured to calculate a system matrix concerning the imaging system based on the general-purpose base vector and the dedicated base vector acquired by the base vector acquisition unit and the spectral characteristic of the imaging system acquired by the system spectral characteristic acquisition unit;

an inverse matrix calculation unit configured to calculate an inverse matrix of the system matrix calculated by the matrix calculation unit;

a coefficient selection unit configured to select coefficients concerning the general-purpose base vector from coefficients of the inverse matrix calculated by the inverse matrix calculation unit; and a multiplication/addition unit configured to calculate a weighting factor concerning the general-purpose base vector based on the coefficients selected by the coefficient selection unit and the image signal.

12. The system according to claim 1, further comprising an identification target selection unit configured to select one subject from a plurality of subjects as identification targets, wherein the base vector acquisition unit acquires a dedicated base vector based on a spectral characteristic of the one subject selected by the identification target selection unit.

13. The system according to claim 1, further comprising a color imaging system selection unit configured to select one color imaging system and one illumination light from a plurality of color imaging systems and a plurality of illumination lights, wherein the system spectral characteristic acquisition unit acquires a spectral characteristic concerning the one color imaging system and a spectral characteristic concerning the one illumination light selected by the color imaging system selection unit as the spectral characteristic of the imaging system.

14. The system according to claim 1, wherein the output signal calculation unit comprises:

a normalization unit configured to normalize the weighting factor concerning the dedicated base vector and the weighting factor concerning the general-purpose base vector calculated by the calculation unit; and an output unit configured to output as the output signal the weighting factor concerning the dedicated base vector and the weighting factor concerning the general-purpose base vector normalized by the normalization unit.

15. The system according to claim 1, wherein the output signal calculation unit comprises:

an emphasis unit configured to emphasize the image signal based on the weighting factor concerning the dedicated base vector and the weighting factor concerning the general-purpose base vector calculated by the calculation unit; and an output unit configured to output as the output signal the image signal emphasized by the emphasis unit.

16. The system according to claim 1, wherein the output signal calculation unit comprises:

a normalization unit configured to normalize the weighting factor concerning the dedicated base vector and the weighting factor concerning the general-purpose base vector calculated by the calculation unit;

a combination unit configured to combine the weighting factor concerning the dedicated base vector and the weighting factor concerning the general-purpose base vector normalized by the normalization unit with the image signal; and an output unit configured to output as the output signal the image signal combined with the weighting factor concerning the dedicated base vector and the weighting factor concerning the general-purpose base vector by the combination unit.

17. The system according to claim 1, wherein the output signal calculation unit comprises:

a normalization unit configured to normalize the weighting factor concerning the dedicated base vector and the weighting factor concerning the general-purpose base vector calculated by the calculation unit; and an output unit configured to output as the output signal the weighting factor concerning the dedicated base vector and the weighting factor concerning the general-purpose base vector normalized by the normalization unit and the image signal.

18. The system according to claim 1, wherein the image signal is an image signal having three bands of red, green, and blue or an image signal having four hands of cyan, magenta, yellow, and green.

19. The system according to claim 1, wherein the known spectral characteristic is a continuous spectral reflectance characteristic for the wavelengths including the wavelengths of the visible range.

20. A computer-readable device having a signal processing program stored thereon, the program being executable to control a computer to perform functions comprising:

acquiring an image signal obtained by image acquisition of subjects including a subject as an identification target having a known spectral characteristic by a color imaging system;

acquiring (i) a dedicated base vector based on the known spectral characteristic of the subject as the identification target having the known spectral characteristic, the known spectral characteristic being a spectral reflectance characteristic for wavelengths including wavelengths of a visible range, and (ii) a general-purpose base vector together with the dedicated base vector, the general-purpose base vector being used in estimation of a spectral characteristic of an arbitrary subject;

acquiring a spectral characteristic of an imaging system including a spectral characteristic concerning the color imaging system and a spectral characteristic concerning illumination light used for image acquisition of subjects by the color imaging system;

calculating a weighting factor concerning the dedicated base vector using the acquired image signal, the acquired dedicated base vector, and the acquired spectral characteristic of the imaging system;

calculating a weighting factor concerning the general-purpose base vector using the acquired image signal, the acquired general-purpose base vector, the acquired dedicated base vector, and the acquired spectral characteristics of the imaging system; and calculating an output signal as an identification result of the subject which is the identification target based on the weighting factor concerning the dedicated base vector and the weighting factor concerning the general-purpose base vector.

21. The computer-readable device according to claim 20, further comprising acquiring a dedicated base vector based on a known spectral characteristic of a subject which is not the identification target.

22. The computer-readable device according to claim 21, wherein the calculating the weighting factor concerning the dedicated base vector comprises:

calculating a system matrix concerning the imaging system on the basis of the acquired dedicated base vector based on the known spectral characteristic of the subject as the identification target, the acquired dedicated base vector based on the known spectral characteristic of the subject which is not the identification target, the acquired general-purpose base vector, and the acquired spectral characteristic of the imaging system;

calculating an inverse matrix of the calculated system matrix;

selecting coefficients concerning the dedicated base vector based on the known spectral characteristic of the subject as the identification target from coefficients of the calculated inverse matrix; and calculating a weighting factor concerning the dedicated base vector based on the known spectral characteristic of the subject as the identification target on the basis of the selected coefficients and the acquired image signal.

23. The computer-readable device according to claim 20, wherein the calculating the weighting factor concerning the dedicated base vector comprises:

calculating a system matrix concerning the imaging system based on the acquired dedicated base vector, the acquired general-purpose base vector, and the acquired spectral characteristic of the imaging system;

calculating an inverse matrix of the calculated system matrix;

selecting coefficients concerning the dedicated base vector from coefficients of the calculated inverse matrix; and calculating a weighting factor concerning the dedicated base vector based on the selected coefficients and the acquired image signal.

24. The computer-readable device according to claim 20, wherein the calculating the weighting factor concerning the general-purpose base vector comprises:

calculating a system matrix concerning the imaging system based on the acquired general-purpose base vector and dedicated base vector and the acquired spectral characteristic of the imaging system;

calculating an inverse matrix of the calculated system matrix;

selecting coefficients concerning the general-purpose base vector from coefficients of the calculated inverse matrix; and calculating a weighting factor concerning the general-purpose base vector based on the selected coefficients and the acquired image signal.

* * * * *